United States Patent
Ito et al.

(10) Patent No.: US 9,976,968 B2
(45) Date of Patent: May 22, 2018

(54) CRACKING DETECTION SYSTEM AND CRACKING DETECTION METHOD

(71) Applicants: Saga University, Saga (JP); Nagasaki University, Nagasaki (JP)

(72) Inventors: Yukihiro Ito, Saga (JP); Kazuhisa Shiki, Saga (JP); Hiroshi Matsuda, Nagasaki (JP); Akira Demizu, Nagasaki (JP)

(73) Assignees: SAGA UNIVERSITY, Saga (JP); NAGASAKI UNIVERSITY, Nagasaki (JP)

( * ) Notice: Subject to any disclaimer, the term of this patent is extended or adjusted under 35 U.S.C. 154(b) by 219 days.

(21) Appl. No.: 15/030,209

(22) PCT Filed: Oct. 17, 2014

(86) PCT No.: PCT/JP2014/077718
§ 371 (c)(1),
(2) Date: Apr. 18, 2016

(87) PCT Pub. No.: WO2015/056790
PCT Pub. Date: Apr. 23, 2015

(65) Prior Publication Data
US 2016/0252464 A1    Sep. 1, 2016

(30) Foreign Application Priority Data
Oct. 18, 2013   (JP) .................. 2013-217722

(51) Int. Cl.
*G01N 21/956*   (2006.01)
*G01N 21/88*    (2006.01)
(Continued)

(52) U.S. Cl.
CPC .............. *G01N 21/956* (2013.01); *G01L 5/00* (2013.01); *G01N 21/8851* (2013.01);
(Continued)

(58) Field of Classification Search
CPC .. G01N 21/956; G01N 21/8851; G01N 25/72; G01N 2021/8893; G01L 5/00; H05B 6/02; H05B 6/36
See application file for complete search history.

(56) References Cited

FOREIGN PATENT DOCUMENTS

| JP | 2001021539 | 1/2001 |
|---|---|---|
| JP | 2003344303 | 12/2003 |

(Continued)

OTHER PUBLICATIONS

International Search Report dated Jan. 20, 2015 From Corresponding International Application No. PCT/JP2014/077718.

*Primary Examiner* — Thai Tran
*Assistant Examiner* — Christopher T Braniff
(74) *Attorney, Agent, or Firm* — Duquette Law Group, LLC

(57) ABSTRACT

There is provided a crack detection system in which a crack can be detected from a strain distribution of a part to be detected of an object. After taking the image of the part to be detected of the detection object by the imaging unit, the heat is applied by the heating unit. Furthermore, image of the part to be detected are taken again and an image analysis unit analyzes the images before and after applying the heat to acquire a strain distribution of the part to be detected, so that the crack can be detected based on difference in a state of strain between a place where the crack exist and the other place. Therefore, taking the images of the part to be detected including its coating layer enables the analysis to progress without removing the coating layer to detect the crack.

23 Claims, 26 Drawing Sheets

(51) Int. Cl.
  *G01N 25/72* (2006.01)
  *G01L 5/00* (2006.01)
  *H05B 6/02* (2006.01)
  *H05B 6/36* (2006.01)
(52) U.S. Cl.
  CPC ............... *G01N 25/72* (2013.01); *H05B 6/02* (2013.01); *H05B 6/36* (2013.01); *G01N 2021/8893* (2013.01)

(56) References Cited

FOREIGN PATENT DOCUMENTS

| | | |
|---|---|---|
| JP | 2004037201 A | 2/2004 |
| JP | 2005345217 | 12/2005 |
| JP | 2006189410 A | 7/2006 |
| JP | 2007024674 A | 2/2007 |
| JP | 2007139653 A | 6/2007 |

NON-PASSING-THROUGH PORTION

CRACKING DETECTION SYSTEM AND CRACKING DETECTION METHOD

TECHNICAL FIELD

The present invention relates to a crack detection method, which permits to confirm an existence of crack in a detection object in a non-destructive manner.

BACKGROUND ART

With respect to steel structures such as a bridge or the like, an appropriate maintenance work is required for these structures so that aged deterioration in load bearing ability and durability of such structures may not reduce the safety of them. Especially, under some circumstances where external forces are repeatedly applied to steel materials of the steel structure, for example, in a bridge to which a load is repeatedly applied along with the passage of vehicles, cracks may occur in places such as welded portions in which stress may easily concentrate, and such cracks may cause an event reducing the safety, such as fracture of the steel material, and accordingly, there is a strong demand to detect early the cracks.

The major conventional ways to detect a crack caused in a steel material of a steel structure may include a magnaflux method, a penetrant testing method and an ultrasonic testing method.

JP 2001-21539 A (Patent Literature 1) discloses an example of the conventional magnaflux method. JP 2003-344303 A (Patent Literature 2) discloses an example of the penetrant testing method. In addition, JP 2005-345217 A (Patent Literature 3) discloses an example of the ultrasonic testing method.

CITATION LIST

Patent Literature

[Patent Literature 1] JP 2001-21539 A
[Patent Literature 2] JP 2003-344303 A
[Patent Literature 3] JP 2005-345217 A

SUMMARY OF INVENTION

Technical Problem

There are the conventional methods of detecting a crack in a steel material as disclosed in the above-mentioned Patent Literatures 1 to 3, respectively, and all of them are useful for detection of a crack, but include troubles in utilization.

The magnaflux method as disclosed in Patent Literature 1 as indicated above is a sensitive method in detection of a crack in a surface portion of a member. However, a portion of the member, which can be magnetized, is limited to a local region, and there is a need to remove a coating layer on the surface of the member, thus reducing work efficiency, and in the case of a large-scaled structure, a long period of time to complete the entire method is required, thus causing problems.

In the penetrant testing method as disclosed in Patent Literature 2 as indicated above, in which penetrant is applied on the surface of a member to make a crack to be detectable, three is also a need to remove a coating layer on the surface of the member in the same manner as the magnaflux method as indicated above, thus requiring much time for carrying out the method, and being not suitable for the testing method for detection in a wide area of an actual structure.

In the ultrasonic testing method as disclosed in Patent Literature 3, a transducer emits an ultrasonic pulse, the ultrasonic pulse is reflected from a defect within a member to cause a reflective wave, such a reflective wave is received and converted into a high-frequency voltage, and then a position of an existing defect and its size can be displayed based on the high-frequency voltage. However, there cannot be provided a sufficient recording performance, a determination of kinds of defects requires much skill and there is a need to take various considerations based on information displayed on a screen, thus reducing work efficiency and causing a problem that an operator may suffer from exhaustion for a work for a long continuous period of time.

In the maintenance work of the steel structure, it is essential to detect early a crack by carrying out an inspection and take immediately an appropriate measure, for example, to carry out a repair work. However, the conventional technical art to detect a crack in a steel structure includes the above-mentioned problems, in workability and work efficiency, of limitation of the detection region to a local one, the need to remove the coating layer, and the like, and accordingly, there is a strong demand to provide a novel crack detection method, which is excellent in workability and a required period of time for detection, and can reduce a detection cost.

An object of the present invention, which has been made to solve the above-mentioned problems, is to provide a crack detection method and a crack detection system to be used in the above-mentioned detection method, in which a crack can properly be detected from a strain distribution of a part to be detected, as acquired without destroying a coating layer of the part to be detected, by applying heat to the part to be detected of a detection object, and analyzing, by a digital image correlation method, images as taken before and after applying the heat to the coating layer of the part to be detected.

Solution to Problem

A crack detection system comprises: an imaging unit that takes an image of an outermost coating surface of a predetermined part to be detected, of a detection object, which part comprises a main body formed of an conductive material and a coating layer formed of a non-conductive material, with which the main body is coated from outside; a heating unit that applies heat to at least surface area of the part to be detected, to increase a temperature of the coating layer to a predetermined temperature by which the coating layer may not degrade, by an induction heating applied to the part to be detected and/or a heat transfer in a vicinity of the part to be detected, along with the induction heating applied to the part to be detected; and an image analysis unit that analyzes two images of the same detection object, which have been taken at different times, to determine strain between the two images in respective positions within a range for detection and acquire a strain distribution within the range for detection; wherein: the imaging unit takes the image of the coating surface of the part to be detected before applying the heat by means of the heating unit and immediately after applying the heat; the image analysis unit determines the strain by the analysis from the two images of the part to be detected, which have taken by the imaging unit before and after applying the heat, in respective positions of the part to be detected, to acquire the strain distribution in the part to be detected; and the strain distribution in the part to be detected includes, in case where a crack exists in the part to be detected, a group of strains in which strains are concentrated almost linearly in a quite different form from other strains around the group of strains in the strain distribution, in response to a small displacement of an area with the crack due to application of the heat.

In the present invention, the imaging unit takes an image of the coating surface of the part to be detected of the detection object, the heating unit applies the heat to the part to be detected, the image of which has been taken, by the induction heating to increase the temperature of the part to be detected, the imaging unit takes again the image of the part to be detected including the coating layer, to which the heat has been applied, and the image analysis unit analyzes the images as taken before and after applying the heat, to acquire the strain distribution in the part to be detected, thus making it possible to detect a crack based on difference in a strain state between a place where the crack exist and the other place. Therefore, taking the images of the part to be detected including its coating layer with the use of the imaging unit enables the analysis to progress without any problems to detect the crack, and the detection can be performed without removing the coating layer from the part to be detected, thus improving the work efficiency of the detection operation. In addition, it is possible to confirm the condition of the part to be detected, by taking the image with the use of the imaging unit in a non-contact manner, there is no influence to the part to be detected, a setting degree of freedom of the part to be detected can be improved, so that the part to be detected can be set so as to carry out an effective detection operation to perform a smooth detection of the crack. Further, the induction heating caused by the heating unit makes it possible to heat directly the part to be detected, without heating the coating layer, to prevent deterioration of the coating layer by heat, and increase the temperature of the part to be detected, in a short period of time, while maintaining the protection of the part to be detected, by the coating layer, thus reducing the operating time to detect the crack.

In the crack detection system according to the present invention, the heating unit may comprise a coil that generates an eddy current in the part to be detected through an electromagnetic induction to generate heat of the part to be detected; and an alternating electric current that has a frequency, which equal to or more than a predetermined frequency, and is capable of heating only a surface area, on a side near the heating unit, of the part to be detected, through a skin effect by the eddy current, to generate a difference in temperature in a thickness direction of the part to be detected, when applying heat, may be applied to the coil to achieve the induction heating of the part to be detected.

In the present invention, application of the alternating electric current having a predetermined high frequency to the coil of the heating unit to achieve the induction heating permits to decrease a penetration depth of the eddy current into the detection object, so as to achieve effectively the induction heating only at the at least surface area of the part to be detected on the side near the heating unit, thus causing a difference in temperature in the thickness direction of the part to be detected, it is possible to provide a state in which a warpage deformation is caused on the detection object in accordance with its thickness, by changing the degree of thermal deformation, with the result that, when heating the surface with a crack, a tensile stress having a function of increasing a crack width due to the warpage is caused, and when heating the opposite surface to the surface with a crack, a compression stress having a function of closing the crack due to the warpage is caused, thus causing the noticeable strain in the area with the crack, thus making it possible to cause the strain, which is more noticeable than that in case where a detection object is thermally deformed uniformly in a thickness direction, to provide a clearer recognition of a group of strains indicating the crack in the strain distribution obtained by the analysis of the image as taken, thus permitting to perform a crack detection in a more reliable and rapid manner.

The crack detection system according to the present invention may further comprise: a display unit that display the strain distribution, which has been acquired by the image analysis unit, as an image in a form of a strain distribution chart, which is associated with an image region of the part to be detected; and wherein: the display unit makes the group of strains in which at least the strains are concentrated almost linearly in the image of the strain distribution chart, clearly distinguishable in a displayed state from the other strains around the group of strains to display the group of strains in a visually distinguishable manner.

In the present invention, the display unit displays the strain distribution, and in case where the part to be detected includes the crack, there is displayed the image including a clear indication of the group of strains as being concentrated linearly, which corresponds to the crack and is clearly distinguishable from the other strains around them. It is therefore possible for an operator who carries out the detection operation to recognize visually the crack on the display unit to understand surely the existence of the crack, thus achieving the detection of the crack without wasting time at a site of work.

In the crack detection system according to the present invention, the imaging unit may comprise one or more portable cameras; and the image analysis unit may comprise a transportable computer that is capable of receiving input data of images from the camera serving as the imaging unit, and that utilizes a predetermined program to determine the strain in respective positions of the part to be detected, from the two images of the part to be detected, which have taken by the imaging unit before and after applying the heat, by an analysis of a digital image correlation method, so as to perform a function of acquiring the strain distribution in the part to be detected.

In the present invention, the imaging unit comprises one or more cameras and the image analysis unit comprises a transportable computer. It is therefore possible to provide configurations of the imaging unit and the image analysis unit in a simple manner, so as to carry these units in a site of work of detecting the crack or carry them out from there and to install them for detection or remove them after completion of detection, with no difficulty, thus improving efficiency of detection operation. In addition, the camera serving as the imaging unit permits to adjust flexibly a shooting range, thus making it possible to set easily the shooting range, i.e., the part to be detected, as a suitable range for a situation. In case where, the range for the part to be detected is set as the maximum wide range in an area where the heating unit can apply heat, a single detection operation may provide a detection of a crack in a wide area, thus permitting to achieve effectively the detection of crack.

In the crack detection system according to the present invention, the imaging unit may be placed in a predetermined position distant from the part to be detected, by a distance longer than that between the part to be detected and a position of the heating unit when performing the induction heating, so as to take the image of the part to be detected, without a relative movement of the imaging unit to the part to be detected, before and after applying the heat to the part to be detected, by means of the heating unit.

In the present invention, the imaging unit is placed, relative to the part to be detected, in the position distant from the position where the heating step is achieved by the heating unit, so as to prevent the heating unit and the imaging unit from coming originally into contact with each other, when applying the heat to the part to be detected, by the heating unit, thus providing a situation in which the image-taking step can be carried out without the movement of the imaging unit relative to the part to be detected, before and after applying the heat to the part to be detected, and fixing the shooting range by the imaging unit. It is therefore possible to acquire, with a high degree of accuracy, the image of the part to be detected, which can be taken by the imaging unit, when acquiring the image before and after applying the heat to the part to be detected, and making detectable the crack of the part to be detected, thus permitting to acquire the strain distribution in a fine mode by the analysis of the image, detect accurately even smaller cracks in the part to be detected and ensure a high degree of detection accuracy.

In the crack detection system according to the present invention, the imaging unit and the heating unit may be connected to each other so as to be movable in a united body relative to the part to be detected; the heating unit may be adapted to heat the part to be detected, from a side in a vicinity of the part to be detected on a side where the imaging unit is placed; and the imaging unit and the heating unit may be movable relative to the detection object so as to change sequentially positions of the part to be detected, at which steps of taking the image and applying the heat can be performed, respectively.

In the present invention, the imaging unit and the heating unit are connected to each other into the united body so that, while the imaging unit takes the image of the part to be detected, and the heating unit applies the heat to the part to be detected, from the same side as the imaging unit, to acquire the images of the part to be detected, before and after applying the heat to it, permitting to make detectable the crack of the part to be detected, these units are moved to achieve repeatedly the similar detection for the subsequent part to be detected. Once the shooting range by the imaging unit and the heating range by the heating unit are adjusted and set finally, a mere movement of these units without adjusting these ranges may suffice for the subsequent detections for the part to be detected, thus permitting to achieve effectively the detection of the crack with the same degree of detection accuracy across a wide area of the part to be detected, and avoid the need to carry out repeatedly the installing operation of the imaging unit and the heating unit for every parts to be detected, thus improving efficiency of the detection operation.

A crack detection method according to the present invention comprises the steps of: taking, by a predetermined imaging unit, an image of an outermost coating surface of a predetermined part to be detected, of a detection object, which part comprises a main body formed of an conductive material and a coating layer formed of a non-conductive material, with which the main body is coated from outside; applying heat to the part to be detected, the image of the coating surface of which has been taken, to increase a temperature of the coating layer to a predetermined temperature by which the coating layer may not degrade, by an induction heating applied to the part to be detected by means of a predetermined heating unit and/or a heat transfer in a vicinity of the part to be detected, along with the induction heating applied to the part to be detected; taking an image of the coating surface of the part to be detected to which the heat has been applied, by means of the imaging unit once again; and determining, by a predetermined image analysis unit, strain by analysis from two images of the part to be detected, which have taken by the imaging unit before and after applying the heat, in respective positions of the part to be detected, to acquire a strain distribution in the part to be detected; and wherein: the strain distribution in the part to be detected includes, in case where a crack exists in the part to be detected, a group of strains in which strains are concentrated almost linearly in a quite different form from other strains around the group of strains, in the strain distribution in response to a small displacement of an area with the crack due to application of the heat.

In the present invention, after taking the image of the part to be detected, for the detection of a crack of the detection object by the imaging unit 10, the heat is applied to the part to be detected, by the heating unit, so as to cause a strain, which may forcibly open or close the crack, and change of the part to be detected, by heat, is also caused on the other surface side through the outer coating surface of the part to be detected, which is to be moved together with the part to be detected. Accordingly, the imaging unit takes images of every portions of the coating surface of the part to be detected, which has been heated, the image analysis unit analyzes the images before and after applying the heat to acquire a strain distribution of the part to be detected, so that the crack can be detected based on difference in a state of strain between a place where the crack exist and the other place. Therefore, taking the images of the part to be detected including its coating layer enables the analysis to progress without any problems to detect the crack, and the detection can be performed in a non-destructive manner without removing the coating layer from the part to be detected, thus improving the work efficiency of the detection operation. In addition, it is possible to confirm the condition of the part to be detected, by taking the image with the use of the imaging unit in a non-contact manner, there is no influence to the part to be detected, a setting degree of freedom of the part to be detected can be improved, so that the part to be detected can be set so as to carry out an effective detection operation to perform a smooth detection of the crack. Further, the induction heating caused by the heating unit makes it possible to heat directly the part to be detected, without heating the coating layer, to prevent deterioration of the coating layer by heat, and increase the temperature of the part to be detected, in a short period of time, while maintaining the protection of the part to be detected, by the coating layer, thus reducing the operating time to detect the crack.

In the crack detection method according to the present invention, a depth of the crack or existence of penetration of the crack may be detected from a magnitude of strain for the group of strains in which the strains are concentrated almost linearly, in the strain distribution in the part to be detected, based on a relationship between a depth of a crack in a body formed of a same material as the detection object or the part to be detected of the detection object and a magnitude of the strain in the strain distribution corresponding to a position of the crack, both of which have previously been acquired.

The magnitude of strain on the surface, which is caused when applying the heat, becomes large with increased amount of thickness in the detection object, and in case where the crack passes completely through to the other side, the strain in each of tensile and compression directions becomes the largest, and a magnitude of strain in a group of strains indicating the crack has a similar tendency also in the strain distribution, which has been acquired from the images as taken when before and after applying the heat. In the present invention, by acquiring previously the strain distribution from the images, as taken before and after applying the heat, of a certain surface and the opposite surface to which the crack reaches, in a predetermined area, which include, for example, the crack passing partially through to the other side, of the detection object itself, or a body formed of the same material as the part to be detected, of the detection, and by confirming the magnitude of strain in each of a passing-through portion of the crack and a non-passing-through portion of the crack to determine a relationship of them, it is therefore possible to determine the depth of the crack based on the magnitude of strain, even for a group of strains indicating the crack in the strain distribution of the part to be detected, and detect easily an existence of the passing-through portion of the crack in the part to be detected and the crack depth, based on the strain distribution, thus saving many steps to measure for every cracks and achieving confirmation of the condition of the crack in a short period of time.

DESCRIPTION OF EMBODIMENTS (First Embodiment of the Present Invention)

Figure 1:
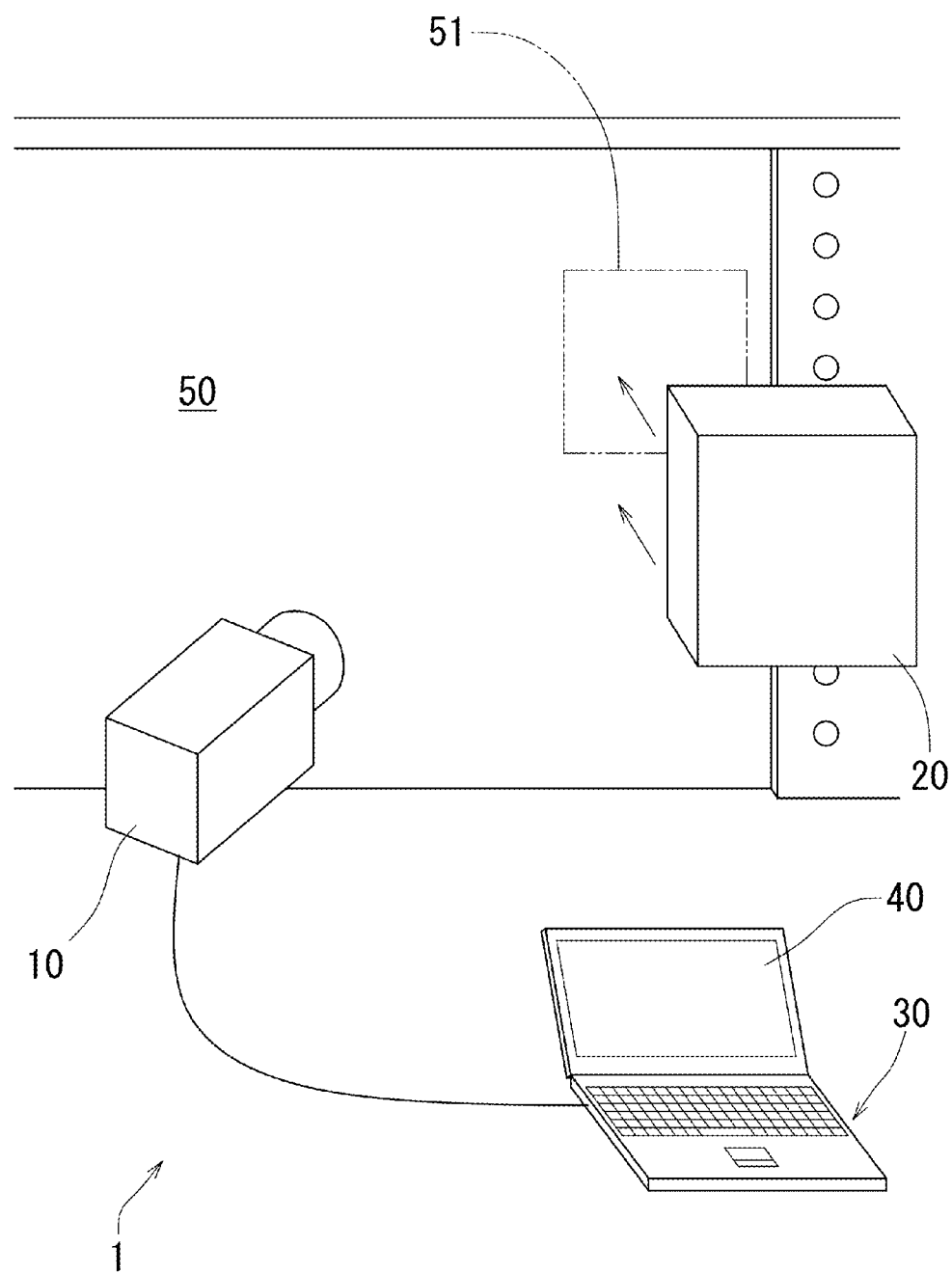
FIG. 1 is a configuration diagram of a crack detection system according to the first embodiment of the present invention.
Figure 2:
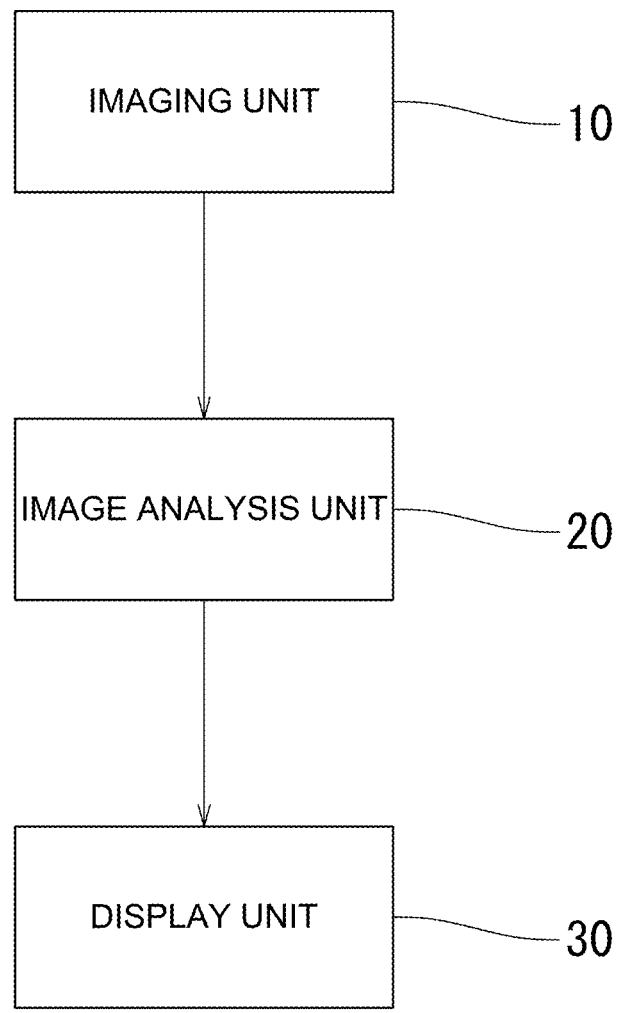
FIG. 2 is a block diagram of the crack detection system according to the first embodiment of the present invention.

Now, a crack detection system according to the first embodiment of the present invention will be described below with reference to FIG. 1 to FIG. 3 as indicated above. The embodiment of the present invention will be described as an example in which a detection object is a structure such as a bridge or the like as made of steel and a part to be detected is a predetermined part of the steel covered with a coating layer (a coating film) applied by a coating method.

The crack detection system 1 utilizing a crack detection method according to the embodiment of the present invention as shown in each of these drawings comprises an imaging unit 10 that takes an image of the outermost coating surface of a predetermined part 51 to be detected, of a detection object 50, which is coated with a coating layer 53 from outside, a heating unit 20 that applies heat to the part 51 to be detected, by an induction heating, an image analysis unit 30 that analyzes two images of the coating film of the above-mentioned part 51 to be detected, which have taken by the imaging unit 10 before and after applying the heat to the coating film, by an analysis of a digital image correlation method, to acquire a stain distribution caused in the part 51 to be detected, by applying the heat, and a display unit 40 that displays the strain distribution as acquired by the image analysis unit 30, in association with an image region of the part to be detected.

The above-mentioned imaging unit 10, which is a known camera of taking an image of a subject, is capable of outputting information (data) on images as taken to the image analysis unit 30. The single imaging unit 10 or a pair of imaging units 10 is placed stationarily in the vicinity of the detection object 50 so as to be directed to the part 51 to be detected of the detection object 50 to take an image of the part 51 to be detected. Use of the single imaging unit can provide an image as taken of the part 51 to be taken, from which a two-dimensional strain distribution can be obtained by the image analysis unit 30. Use of the pair of imaging units to take images from the different positions can provide an image as taken of the part 51 to be taken, from which a three-dimensional strain distribution can be obtained by the image analysis unit 30.

The imaging unit 10 is placed stationarily in a predetermined position, which is distant from the part 51 to be detected, by a distance longer than that between the part 51 to be detected and a position of the heating unit 20 when applying the heat, so as to take the image of the part 51 to be detected, without a movement of the imaging unit to the part 51 to be detected, before and after applying the heat to the part 51 to be detected, by means of the heating unit 20.

The detection object 50 is composed of a main body 52 made of steel and a coating layer 53, which is non-conductive, made of a different material from the main body, and more specifically, with which the main body is coated from outside by applying a synthetic resin coating composition to the main body. For a predetermined part of the main body made of steel, as the part to be detected, the imaging unit 10 is directed to the detection object to take an image without removing the outermost coating layer 53, not to obtain the image of the part to be detected, itself, but to obtain the image of the coating layer. A step of taking the image for the part 51 to be detected, by the imaging unit 10 is carried out at the timing of before and after applying the heat to the part to be detected. The step of taking the image after applying the heat is carried out before the temperature of the coating film 53 changes due to transfer of heat from the part to be detected and the coating layer itself deforms due to the temperature change.

The above-mentioned heating unit 20, which applies heat to the part 51 to be detected, as an object to be heated, by an induction heating, is a known device in which a heating coil (not shown) for generating an eddy current in the object to be heated, to generate heat of it, is placed along a flat top plate, and an detailed description of it will be omitted.

In the heating step, the top plate of the heating unit 20 is placed in the vicinity of the part to be detected in a flat form and kept at this position, and energization of the heating coil generates an eddy current in the part to be detected, formed of steel, by en electromagnetic induction so that the part to be detected is in a heat generating state by Joule heat. The steel material, which is a current-carrying material, enables the predetermined part serving as the part to be detected, to be heated by an induction heating by the heating unit 20, without any adverse influence on the coating layer on the surface of the part to be detected. The coating layer 53 with which the part 51 to be detected is coated is non-conductive and non-magnetic, and not detrimental to an electromagnetic induction in the part 51 to be detected, and elastically deformable, so as to be capable of moving along with a thermal deformation of the part 51 to be detected, while maintaining a close contact state with the surface of the part 51 to be detected.

Due to a nature of the induction heating, this heating unit 20 can provide an improved higher heating efficiency with a decreased distance between the heating unit and the part 51 to be detected, serving as the object to be heated. However, there is no need to bring the heating unit in contact with the part 51 to be detected, and the heating step can be carried out from a position distant from it, thus making it possible to provide a detection system in a non-contact manner, without any influence on the surface of the part to be detected.

The above-mentioned image analysis unit 30 analyzes two images of the same detection object, which have been taken at different times, to determine strain between the two images in respective positions within a range for detection, by a known digital image correlation method, and acquire a strain distribution within the range for detection. More specifically, the image analysis unit determines the strain, which has been caused by applying the heat to the part to be detected, by the above-mentioned analysis from the two images of the part to be detected, which have taken by the imaging unit 10 before and after applying the heat, in respective positions of the part 51 to be detected, to acquire the strain distribution in the part 51 to be detected.

This image analysis unit 30 utilizes a computer provided with a CPU, a memory, input and output interfaces, etc., as a hardware configuration for the computer, so that data for the images as taken can be inputted from the imaging unit 10, thus making it possible to cause the computer to function as the image analysis unit 30 in accordance with a program stored in the memory, etc. of the hardware configuration, and more specifically, a predetermined program, which permits to perform functions of determining the strain, by the analysis through the digital image correlation method, from the two images of the part to be detected, which have taken by the imaging unit 10 before and after applying the heat, in respective positions of the part 51 to be detected, to acquire the strain distribution in the part 51 to be detected. The computer utilized in the image analysis unit 30 may be a microcomputer integrally provided with a CPU, a memory, a ROM, etc.

Designing the image analysis unit 30 in the form of a small-sized computer permits to make the apparatus light-weight and simple, so as to provide effects of carrying it in a site of work of detection and setting it up for detection in an easy manner. When the image analysis unit 30 utilizes the computer, adjustment instructions on the step of taking the image by the imaging unit 10 and the step of applying the heat by the heating unit 20 may be received from the side of the image analysis unit 30, thus avoiding a need to perform respective operations on the respective side of the units, and improving efficiency of the detection operation.

An object whose image is to be taken by the imaging unit 10 is a coating surface of the part 51 to be detected. What is actually analyzed by the image analysis unit 30 are the images of the coating surface of the part 51 to be detected, which have been taken before and after applying the heat, but a small displacement of respective portions of the part 51 to be detected, after applying the heat, is reflected, as it is, on the surface (the coating surface) through the thin coating layer to which the heat has not been applied, and in which properties have not been changed. Therefore, analysis of the images of the coating layer before and after applying the heat permits to process strains of the respective portions of the coating layer as obtained, as strains of the respective portions of the part to be detected, thus providing reliably the strain distribution of the part to be detected.

Figure 3:
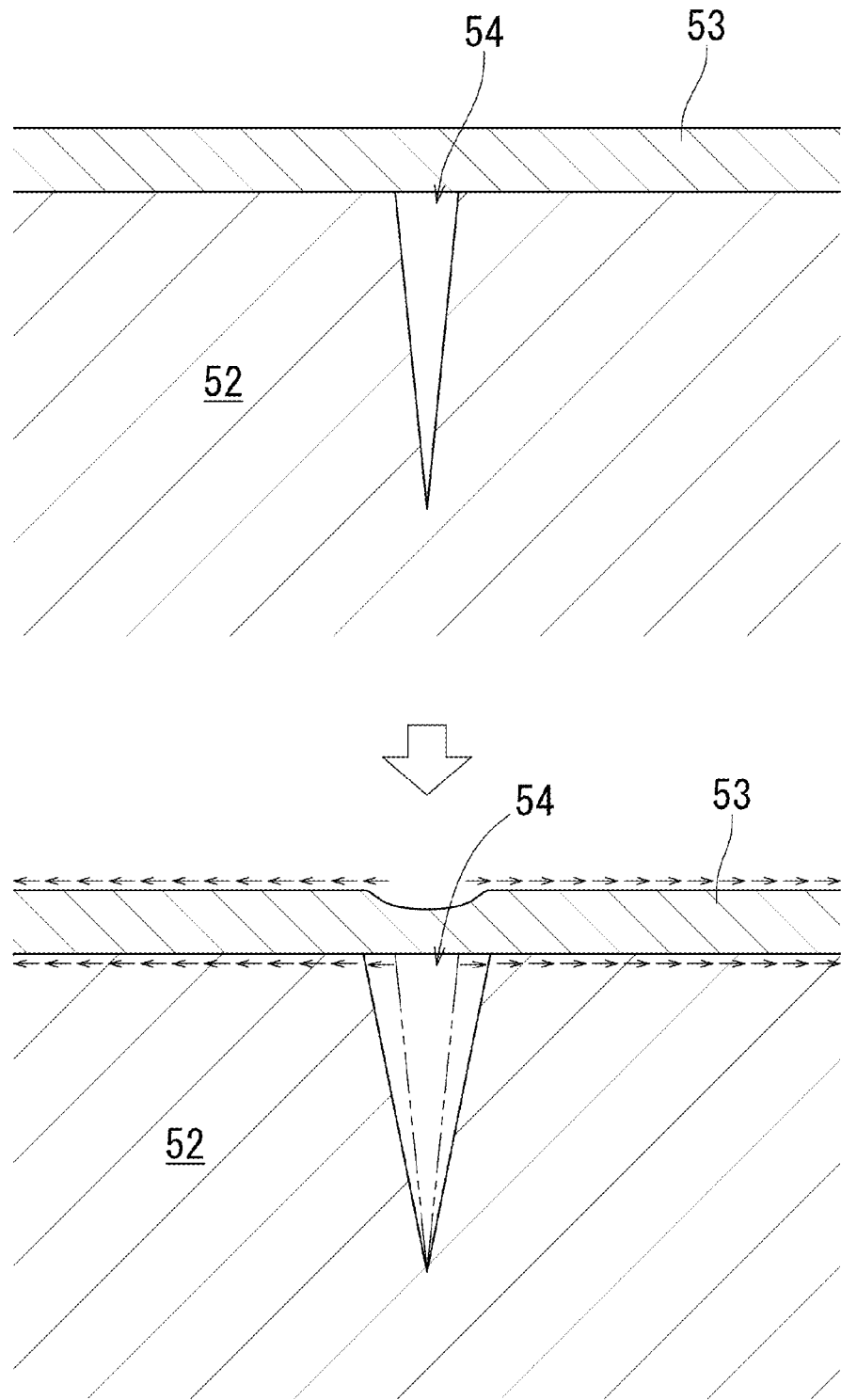
FIG. 3 is a descriptive view of a state of change by applying a heat to a crack portion in a part to be detected, in the crack detection system according to the first embodiment of the present invention.

The strain distribution in the part 51 to be detected, which has been determined by the image analysis unit 30, includes, in case where a crack 54 exists in the part 51 to be detected, a group of strains in which strains are concentrated almost linearly in a quite different in magnitude and direction form from other strains around the group of strains in the strain distribution, in response to a small displacement of an area with the crack 54 due to application of the heat (see FIG. 3). It is therefore possible to detect the crack by displaying the strain distribution in the display unit 40 to enable an observer to recognize visibly it or by extracting a group of almost linear strains as indicated above from the image of the strain distribution by a separate imaging analysis to recognize it as a crack.

Thus, it is possible to detect a crack, and specifically a fatigue crack caused in an area such as a welded-portion where a stress is apt to be concentrated, from the strain distribution. It is also possible to detect the other crack than the fatigue crack, such as an initial defect (welding defect, weld penetration defect, etc.) of a welded portion included in the part to be detected, a crack, which has been caused at the time of manufacture and cannot easily be recognized from outside, of a body as the part to be detected, based on characteristic conditions of the strain, from the strain distribution of the part 51 to be detected, which has been determined by the image analysis unit 30. In the detection, something as detected is determined as whether the fatigue crack, the welding defect, or the like, based on a position where the strain is caused in the part to be detected, which can be derived from the strain distribution. It is highly likely that, for example, strains, which are concentrated in a predetermined position on the strain distribution in response to an area of a detection object, where a stress is concentrated, are a fatigue crack.

For the analysis by the image analysis unit 30 through the digital image correlation method, there is a requirement that the coating layer whose image is to be taken should be a flat surface in which differences in a random pattern exist in a predetermined density. However, a normal substance, which has not been subjected to a specific smoothening process, and specifically, a member of a steel structure, which has a coating layer and in which a predetermined period of time has lapsed from the manufacture while being exposed to air, has originally the above-mentioned surface state, thus permitting to take the image by the imaging unit 10, without carrying out a specific pretreatment. The coating layer may be provided on its surface with a suitable pattern for the imaging analysis, which is formed of a coating material having no adverse influence on the coating layer.

The imaging analysis of the two images as taken, by the image analysis unit utilizes the digital image correlation method. However, the present invention is not limited only to this method, but there may be carried out an imaging analysis that utilizes the other method such as a moiré method, a distance-between-two-points-rate-of-change measurement method, or the like.

The above-mentioned display unit 40 is a known display device for displaying an image, which receives the image data, as inputted, of the strain distribution acquired by the image analysis unit 30, and display the same as an image in a form of a strain distribution chart, which is associated with an image region of the part to be detected, and the detailed description of it will be omitted. This display unit 40 may be a display portion of the computer, which is utilized by the image analysis unit 30, and when the computer is small-sized such as a so-called notebook-size personal computer, it is possible to provide a device having an excellent transportability, an extremely convenience and a good handling property at a site of detection work.

The strain distribution in the part 51 to be detected, which has been determined by the image analysis unit 30, includes, in case where a crack 54 exists in the part 51 to be detected, a group of strains in which strains are concentrated almost linearly in a quite different in magnitude and direction form from other strains around the group of strains in the strain distribution, in response to a small displacement of the area with the crack 54 due to application of the heat. The group of strains naturally has a specific shape in response to the crack. It is therefore possible to confirm an existence of the crack by recognizing visibly the group of strains displayed in the display unit 40 by an observer, and to analyze the images as taken by the image analysis unit 30, thus performing a rapid detection of crack.

The display unit 40 is preferably configured to indicate a magnitude of strain in a predetermined position specified by coordinate values in different display modes in color, etc., corresponding to the magnitude of the strain, respectively, in the image as displayed, so as to permit to display the group of strains indicating the crack in a distinctively visible manner from the other strains around the group of strains.

Now, description will be given below of a crack detection method utilizing the crack detection system according to the embodiment of the present invention. There is the assumption that the imaging unit 10 is placed so as to capture the predetermined part 51 to be detected of the detection object 50, in its scope of imaging, and is connected to the image analysis unit 30, which is placed in the vicinity of the imaging unit, and the heating unit 20 is placed in a position in which a heat can appropriately be applied by the heating unit through induction heating so as to avoid adverse effect on the imaging step by the imaging unit 10. Of course, the respective units are appropriately connected to an electric power source so as to be operable.

First, the image of the part 51 to be detected of the detection object 50 is taken by the imaging unit 10, and data of the images as taken are inputted to the computer, which is utilized by the image analysis unit 30. After taking the image, the heating unit 20 is operated to increase the temperature of the part to be detected to a preset temperature, to provide a state in which a strain is caused by heat. When the temperature of the part to be detected reaches the preset temperature, or there has lapsed a predetermined period of time during which the temperature of the part to be detected has been assumed to reach the preset temperature with a sufficient accuracy, the operation of the heating unit 20 is quitted to complete the heating step of the part to be detected. It is preferable to operate the heating unit 20 at this time, while measuring a surface temperature distribution of the part to be detected through a thermography measurement to confirm accurately the temperature of the part to be detected.

Immediately after this step, the image of the part 51 to be detected of the detection object 50 is taken again by the imaging unit 10, and data of the images as taken are inputted to the computer, which is utilized by the image analysis unit 30. Then, the image analysis of the images as taken before and after applying the heat is carried out through a digital image correlation method to obtain the strain distribution in the imaging analysis device 30, and such a strain distribution is indicated in the display screen serving as the display unit 40.

An operator watches the display unit 40 to confirm whether or not a strain variation different from the surrounding appears in a state in which strains are concentrated almost linearly in a part of the strain in the strain distribution of the part 51 to be detected, and if such a strain variation is caused, he/she determines this part as a crack.

In the crack detection system according to the embodiment of the present invention, after taking the image of the part 51 to be detected, for the detection of a crack of the detection object 50 together with the coating layer 53 on its surface by the imaging unit 10, the heat is applied to the part to be detected, by the heating unit, so as to cause a strain, which may forcibly open or close the crack 54, and change of the part to be detected, by heat, is also caused on the other surface side through the outer coating surface of the part to be detected. Accordingly, the imaging unit 20 takes again images of every portions of the coating surface of the part to be detected, which has been heated, the image analysis unit 30 analyzes the images before and after applying the heat through a digital image correlation method to acquire a strain distribution of the part 51 to be detected, so that the crack can be detected based on difference in a state of strain between a place where the crack exist and the other place. Therefore, taking the images of the part 51 to be detected including its coating layer enables the analysis to progress without any problems to detect the crack, and the detection can be performed in a non-destructive manner without removing the coating layer 53 from the part to be detected, thus improving the work efficiency of the detection operation. In addition, it is possible to confirm the condition of the part 51 to be detected, by taking the image with the use of the imaging unit in a non-contact manner, there is no influence to the part 51 to be detected, a setting degree of freedom of the part 51 to be detected can be improved, so that the part 51 to be detected can be set so as to carry out an effective detection operation to perform a smooth detection of the crack. Further, the induction heating caused by the heating unit 20 makes it possible to heat directly the part to be detected, without heating the coating layer 53, to prevent deterioration of the coating layer by heat, and increase the temperature of the part to be detected, in a short period of time, while maintaining the protection of the part to be detected, by the coating layer, thus reducing the operating time to detect the crack.

In the crack detection system according to the above-mentioned embodiment of the present invention, the system is described as being configured so that the detection object 50 is the steel structure and the crack detection is carried out for the steel material 52 covered with the coating layer on its surface, as the part to be detected of the detection object. However, the present invention is not limited only to such an embodiment, the part to be detected of the detection object may be formed of other metal than steel, or a current-carrying material other than metal, for example, a part formed of carbon fiber, as long as they are capable of being subjected to an induction heating by the heating unit, and namely electrically conductive. Also in a composite material containing such an electrically conductive material, for example, a body formed of fiber-reinforced plastic (FRP) containing metallic fiber or carbon fiber, the temperature of such a material can be increased from the portion, as an origination, of the electrically conductive material by the induction heating. Accordingly, a structure including such a body may be used as the part to be detected.

In the crack detection system according to the above-mentioned embodiment of the present invention, the heating unit 20 is described as being configured so that the heating coil is placed along the predetermined flat plane and an effective induction heating can be carried out when a specific portion of the coil is close to the flat part 51 to be detected. However, the present invention is not limited only to such an embodiment, the heating coil can be used for heating the other shape than the flat plane of the part to be detected, by changing the shape and position of the heating coil, for example by forming the heating coil by winding a wire for the coil in a different three-dimensional shape. More specifically, the heating coil may be flexible so as to be suitable for a various shape of the part to be detected.

In the crack detection system according to the above-mentioned embodiment of the present invention, it is described that the crack can be detected by providing the display unit 40 for displaying the strain distribution acquired by the image analysis unit 30 in the form of image and confirming an existence of the crack from the strain distribution as the displayed image by the operator. However, the present invention is not limited only to such an embodiment, the strain distribution of the part to be detected, which has been acquired through the analysis of the image as taken, by the image analysis unit may be processed as data by another analysis unit, without being subject to any additional processing, so as to detect the crack based on features obtained as data, such as an existence of strain data indicating the crack in a predetermined coordinate space corresponding to the part to be detected, thus permitting to perform an automatic detection of the crack, and to carry out the crack detection even in an observers absence.

In the crack detection system according to the above-mentioned embodiment of the present invention, the image analysis unit 30 is described as performing the imaging analysis of the images, as taken, before and after applying the heat, of the surface of the coating layer of the part 51 to be detected, and acquiring the strain distribution of the part 51 to be detected, thus permitting to detect the crack based on a state in which strains are concentrated almost linearly in the strain distribution. In addition, it is also possible to perform a non-destructive detection of deterioration of a coating layer applied on the surface of the detection object, corresponding to an area, corrosion in the inside of the body, and/or occurrence of rust, from the strain distribution, which includes additional strain area different in magnitude and direction from other strains around them, in addition to the group of strains in which the strains are concentrated almost linearly, in the same manner as the crack detection as mentioned above.

For example, in case where the coating layer applied on the surface of the part to be detected of the steel material has lost adhesion and has been "peeled off", even when the steel material is heated by an induction heating, a small displacement of the respective areas of the steel material due to a thermal deformation does not appear on the surface of the coating layer as peeled, with the result that a value of strain obtained from the analysis becomes very small. Thus, the deterioration of the coating layer can be detected by enabling an observer to confirm visibly an area with such a small value of strain in the strain distribution displayed by the display unit or extracting the area with the small vale of strain from the image of the strain distribution by another imaging analysis.

In an area where a "floating" occurs in the coating layer, an air layer exists between the coating layer and the steel material due to the floating. When the part to be detected is heated through an induction heating by the heating unit to increase its temperature, in the same manner as in the crack detection as mentioned above, the air layer between the coating layer and the steel material expands through a heat transfer from the steel material having the increased temperature, so as to extend the surface of the coating layer, thus causing a small displacement. Thus, the surface of the coating layer in the area with the air layer appears as an area having a large tensile stress in the strain distribution as acquired by the analysis of the images as taken before and after applying the heat, thus making it possible to detect appropriately the floating of the coating layer based on the state of strain in the strain distribution.

Also in an area where the inside of the steel material corrodes due to occurrence of a loose scale, thus breaking a bond of the coating layer to the surface of the steel material, a small displacement of the respective areas of the steel material, which has been heated through an induction heating and deformed, does not appear on the surface of the coating layer, with the result that a value of strain obtained from the analysis becomes very small. Thus, such a state can be detected in this manner. In case where the steel material is provided on its surface with red rust, a magnetic property becomes weak due to such red rust. Accordingly, the area with the red rust is not sufficiently heated through the induction heating, and a thermal deformation of the steel material becomes small, with the result that a value of strain obtained by the analysis of the surface of the coating layer in this area becomes smaller, leading to a larger difference from the surrounding strains and enhancing distinguishability.

It is possible to provide a defect detection system for the surface of the detection object, not limited only to the crack detection, which permits to perform, together with the above-mentioned crack detection, a detection of the "peeled of", "floating" of the coating layer on the surface of the detection object, or the rust in the inside of the steel material, thus permitting to confirm an existence of a plurality of defects by only one detection utilizing the above-mentioned system, applied to the detection object, and to perform an effective detection of such defects and take countermeasures.

In the crack detection system according to the above-mentioned embodiment of the present invention, it is described that an existence of crack can be detected from the state of strain in the strain distribution of the part 51 to be detected, as acquired by the analysis of the images as taken. In addition, a depth of the crack or existence of penetration of the crack may be detected from a magnitude of strain for the group of strains in which the strains are concentrated almost linearly, in the strain distribution in the part to be detected, based on a relationship between a depth of a crack in a body formed of a same material as the detection object or the part to be detected of the detection object and a magnitude of the strain in the strain distribution corresponding to a position of the crack, both of which have previously been acquired.

The magnitude of strain on the surface, which is caused when applying the heat, becomes large with increased amount of thickness in the detection object, and in case where the crack passes completely through to the other side, the strain in each of tensile and compression directions becomes the largest, and a magnitude of strain in a group of strains indicating the crack has a similar tendency also in the strain distribution, which has been acquired from the images as taken when before and after applying the heat.

In the present invention, by acquiring previously the strain distribution from the images, as taken before and after applying the heat, of a certain surface and the opposite surface to which the crack reaches, in a predetermined area, which include, for example, the crack passing partially through to the other side, of the detection object itself, or a body formed of the same material as the part to be detected, of the detection, and by confirming the magnitude of strain in each of a passing-through portion and a non-passing-through portion of the crack to determine a relationship of them, it is therefore possible to determine the depth of the crack based on the magnitude of strain, even for a group of strains indicating the crack in the strain distribution of the part to be detected.

In this case, it is possible to detect easily an existence of the passing-through portion of the crack in the part to be detected and the crack depth, based on the strain distribution of the part to be detected, thus saving many steps to measure for every cracks and achieving confirmation of the condition of the crack in a short period of time.

Figure 4:
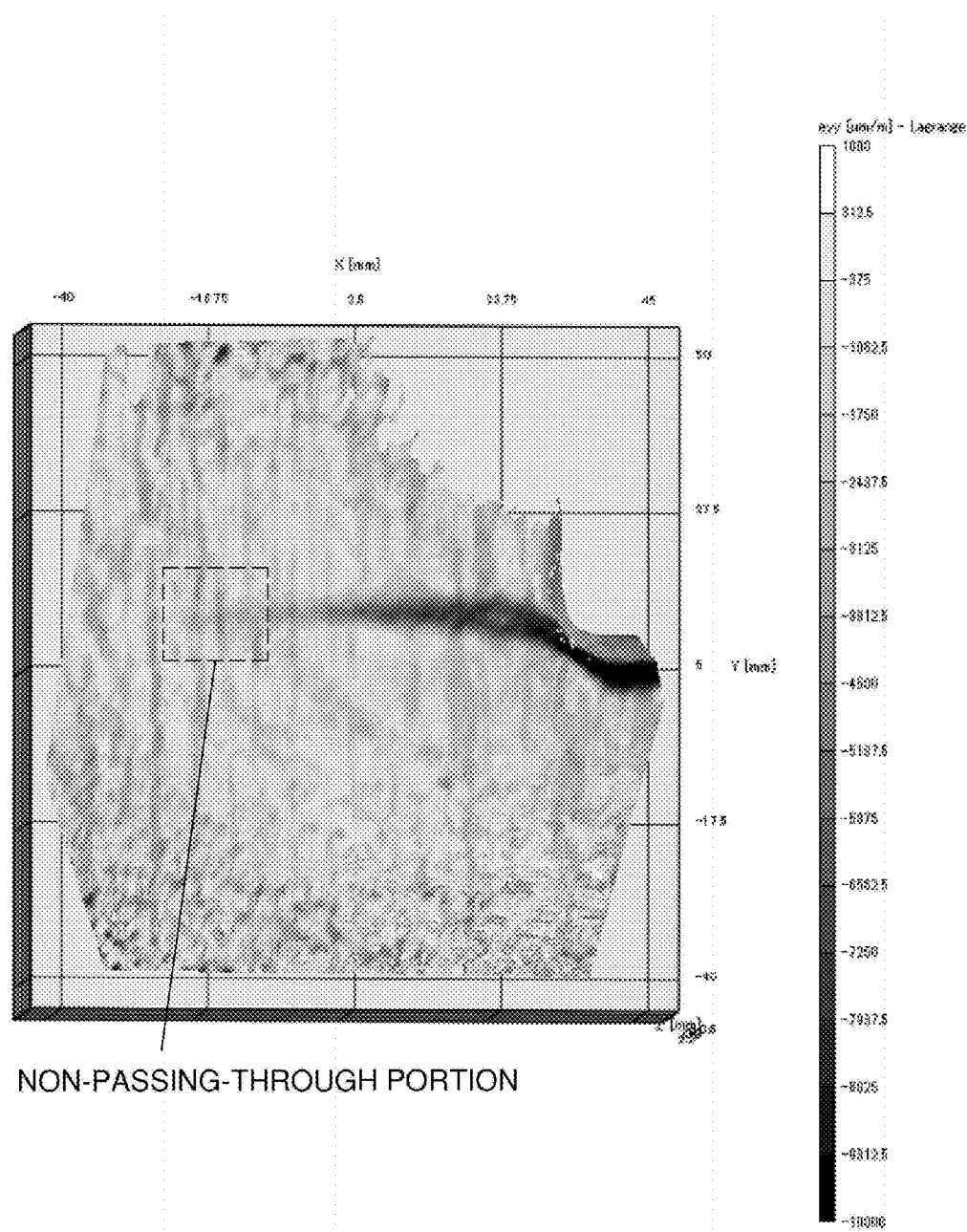
FIG. 4 is a descriptive view of a strain distribution image of a predetermined part to be detected, which includes a crack in the first detection object, as obtained by the crack detection system according to the first embodiment of the present invention.
Figure 5:
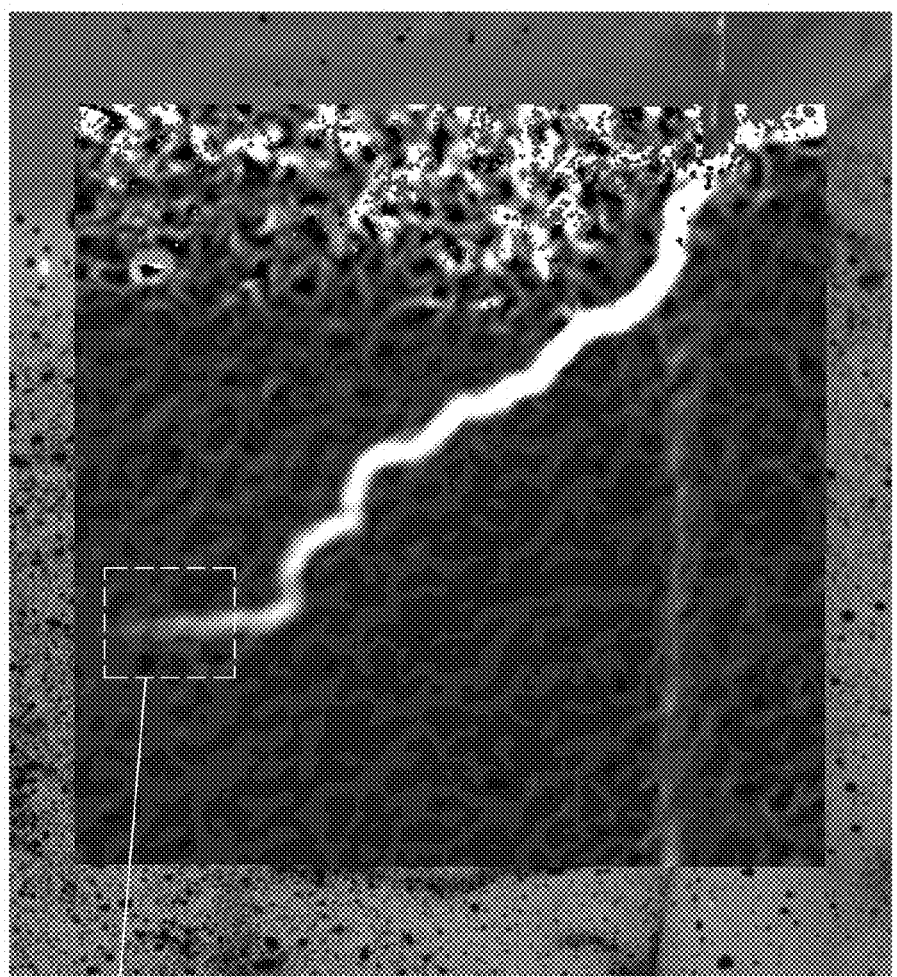
FIG. 5 is a descriptive view of a strain distribution image of a predetermined part to be detected, which includes a crack in the second detection object, as obtained by the crack detection system according to the first embodiment of the present invention.

There will be described, as an example, the strain distribution acquired by the analysis of the images as taken of the part to be detected of the actual detection object (see FIG. 4 and FIG. 5). The opposite surfaces of the part to be detected have been subjected to a separate magnetic-particle testing method to confirm the position of the crack and the passing-through portion of the crack and the non-passing-through portion of the crack have confirmed based on the difference in position of the crack on the opposite surfaces of the part to be detected.

The strain distribution as acquired clearly shows a group of strains, which are concentrated almost linearly, indicating the crack. The magnitude of the strain corresponding to the non-passing-through portion of the crack, which is defined by a rectangular frame as shown in a broken line, in the strain distribution is shown to be smaller in comparison with the strain corresponding to the other passing-through portion of the crack. It is therefore understood that the depth of the crack can be estimated from the magnitude of the strain.

(Second Embodiment of the Present Invention)

The crack detection system according to the first embodiment of the present invention is configured in a way that the heating unit 20 applies the induction heating to the part 51 to be detected of the detection object 50, without limiting specifically any heating area. There may be an alternative configuration in which the heating unit 22 applies the induction heating with an alternating electric current having a sufficiently high frequency (for example, several dozen kHz) to the part 51 to be detected, to heat only the surface area, on the side near the heating unit, of the part 51 to be detected.

In this case, the heating unit 22 applies the alternating electric current having the predetermined frequency (for example, 20 kHz), by which only the surface area, on the side near the heating unit, of the part 51 to be detected can be heated through a skin effect by the eddy current, to provide a difference in temperature in the thickness direction of the detection object 50 at the time of applying the heat, to the heating coil 23.

In the present invention, application of the alternating electric current having the high frequency to the heating coil 23 permits to decrease the penetration depth of the eddy current into the detection object 50, so as to achieve effectively the induction heating only at the surface area of the part 51 to be detected on the side near the heating unit, thus causing a difference in temperature in the thickness direction of the detection object 50 and changing a degree of thermal deformation at the respective position in the thickness direction of the direction object.

It is therefore possible to provide a state in which a warpage deformation is caused on the detection object 50 in accordance with its thickness, by changing the degree of thermal deformation, with the result that, when heating the surface with a crack, a tensile stress having a function of increasing a crack width due to the warpage is caused, and when heating the opposite surface to the surface with a crack, a compression stress having a function of closing the crack due to the warpage is caused, thus causing the noticeable strain in the area with the crack, thus making it possible to cause the strain, which is more noticeable than that in case where a detection object 50 is thermally deformed uniformly in a thickness direction, to provide a clearer recognition of a group of strains indicating the crack in the strain distribution obtained by the analysis of the image as taken, thus permitting to perform a crack detection in a more reliable and rapid manner.

The step of taking the images of the part 51 to be detected by the imaging unit after heating the part 51 to be detected, by the heating unit is carried out before the heat transfer from the surface area of the part 51 to be detected, which has been subjected to the induction heating, increases the temperature of the other portion than the surface and the difference in temperature in the thickness direction of the part 51 to be detected disappears.

The strain distribution in the part 51 to be detected, which has been acquired by the analysis of the images as taken includes a group of strains in which strains are concentrated almost linearly in response to a small displacement of an area with the crack due to application of the heat, in the same manner as the first embodiment of the present invention as described above. However, variation of the crack changes and strain's property changes depend on the heating position of the heating unit 22.

Figure 6:
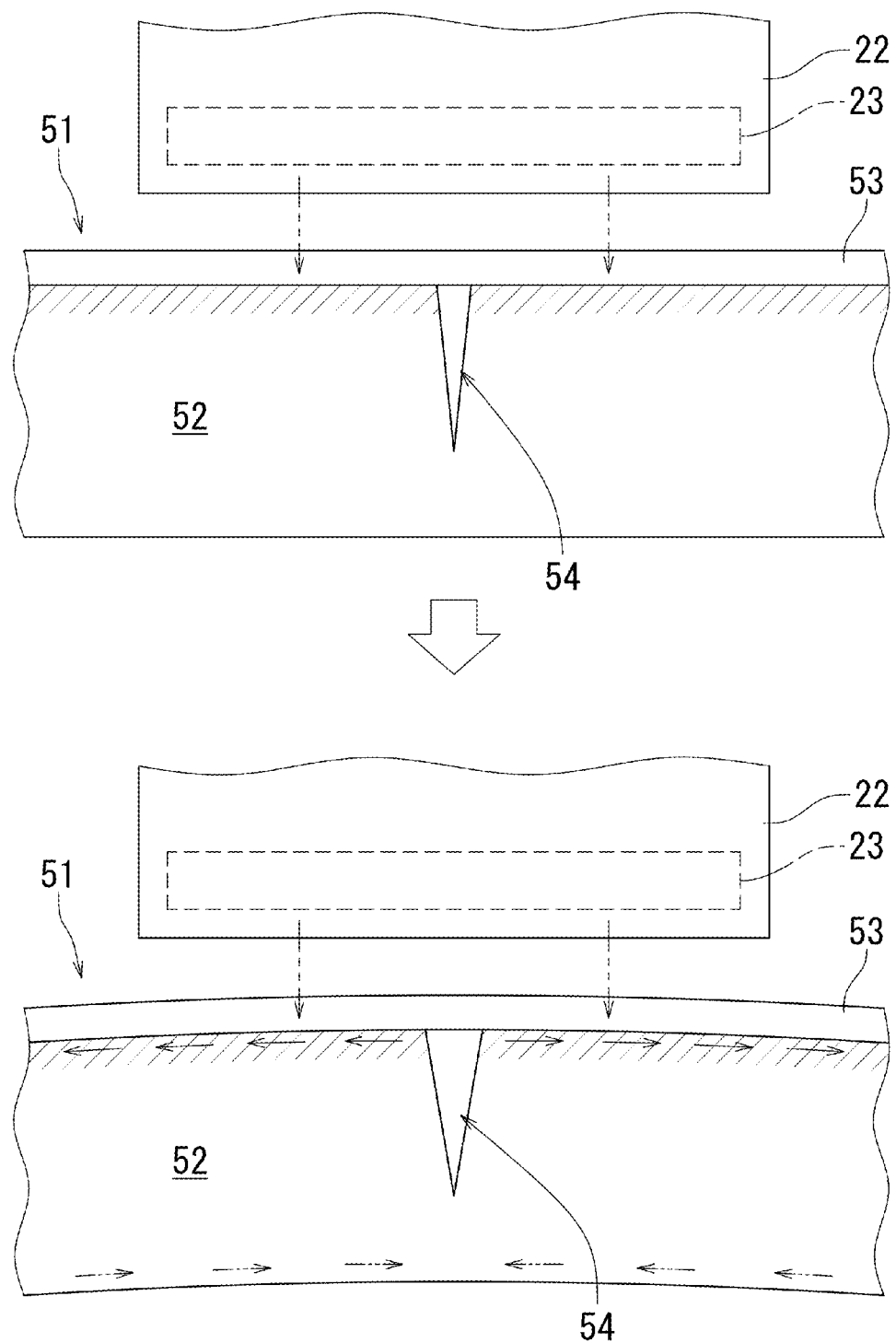
FIG. 6 is a descriptive view of a state of change of a part to be detected, by applying heat to a certain surface including a crack portion in the part to be detected, in the crack detection system according to the second embodiment of the present invention.
Figure 7:
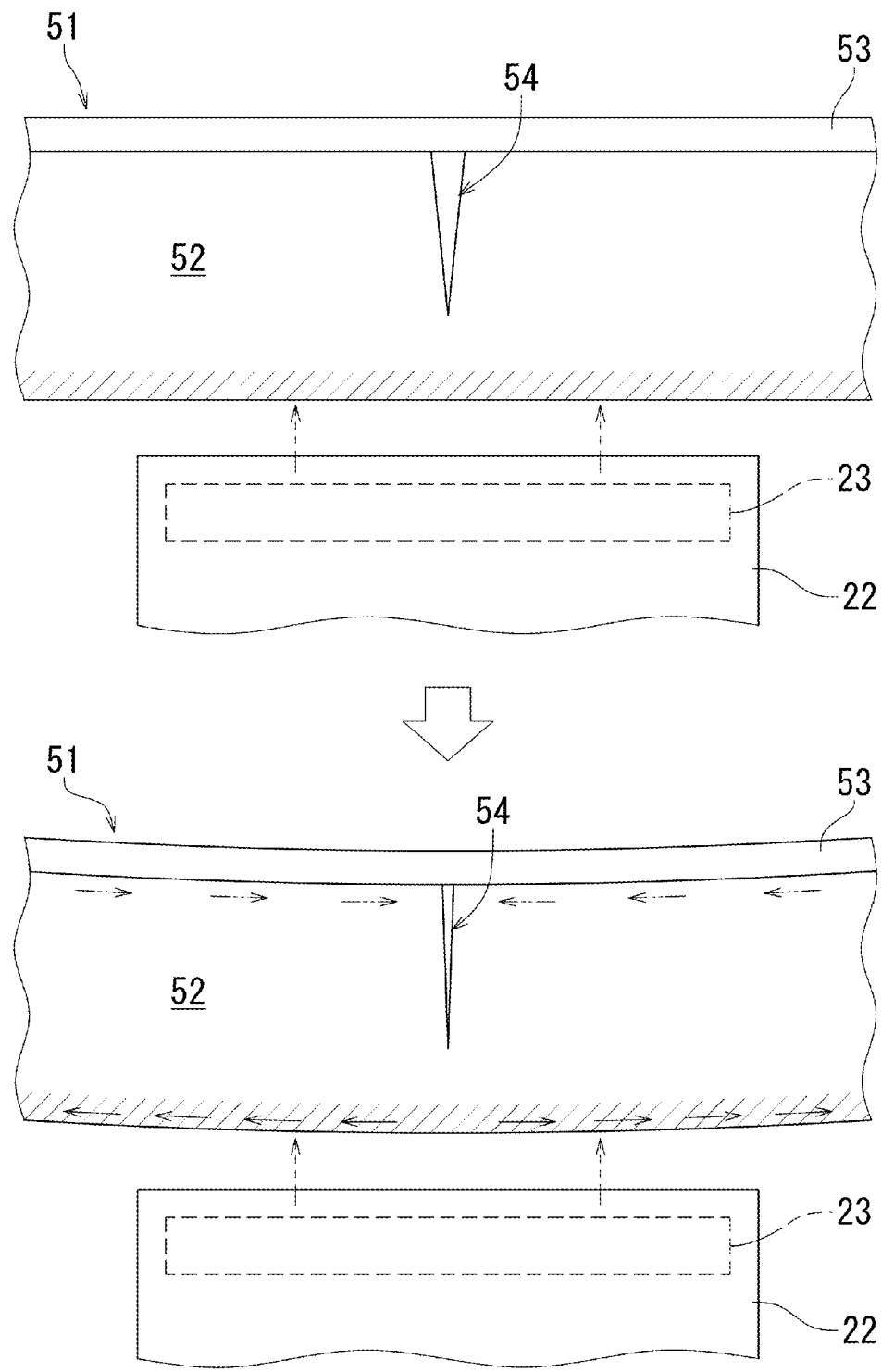
FIG. 7 is a descriptive view of a state of change of a part to be detected, by applying heat to the opposite surface to the certain surface including a crack portion in the part to be detected, in the crack detection system according to the second embodiment of the present invention.

More specifically, when the surface of the part 51 to be detected, including the crack portion is heated by the heating unit 22 (see FIG. 6), there occurs a warpage in a direction in which the surface of the part to be detected extends by heating the above-mentioned surface to a high temperature, and a displacement having a function of opening the crack on the surface, due to a different degree of thermal deformation at the respective position in the thickness direction of the detection object, with the result that the stress is a tensile stress. To the contrary, when the opposite side to the surface of the part 51 to be detected, including the crack portion is heated (see FIG. 7), there occurs a warpage in a direction in which the opposite surface of the part to be detected extends and the surface having the crack contracts relatively, and a displacement having a function of closing the crack on the surface, due to a different degree of thermal deformation at the respective position in the thickness direction of the detection object, with the result that the stress is a compression stress.

(Third Embodiment of the Present Invention)

Figure 8:
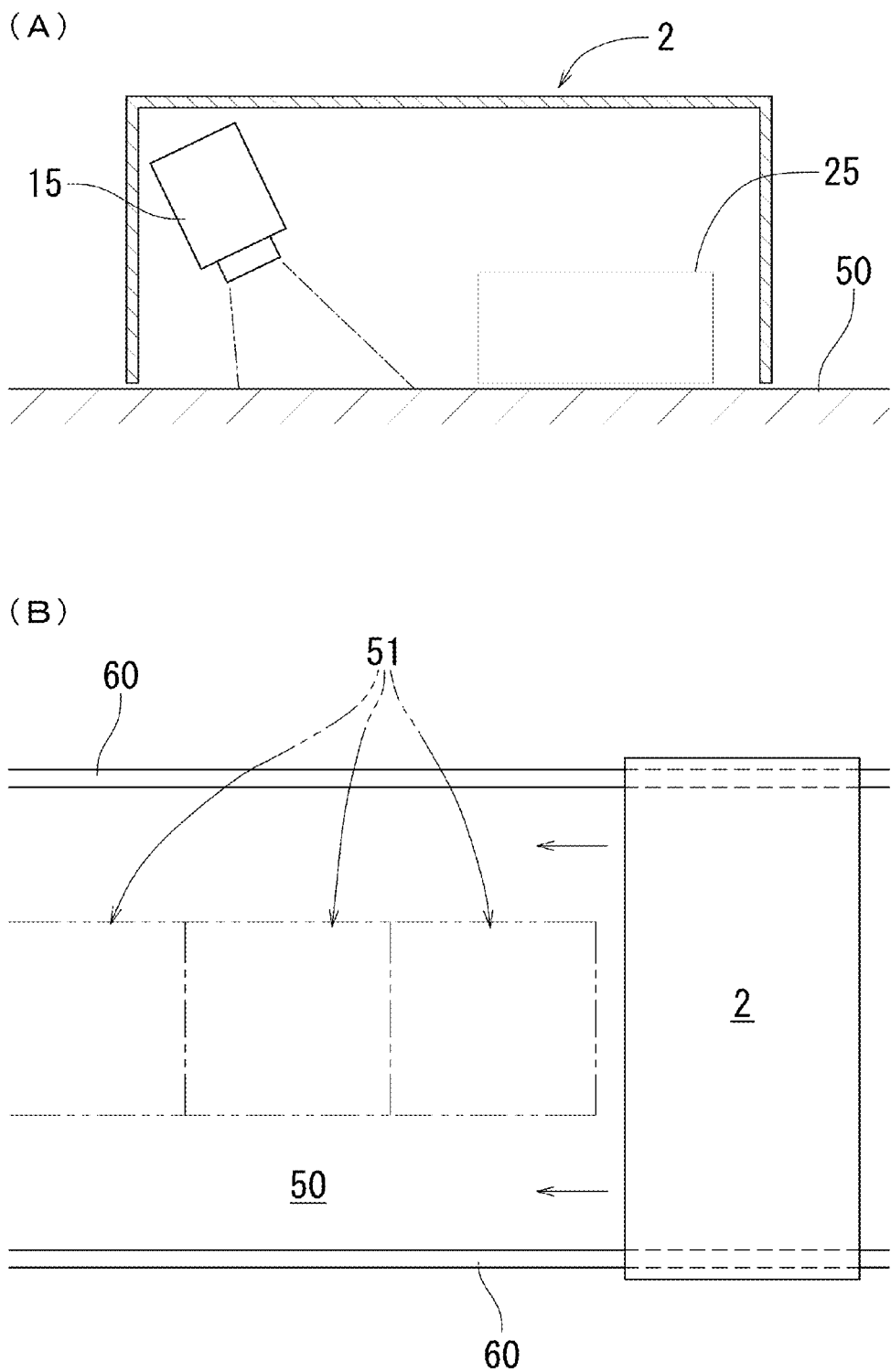
FIG. 8 includes a descriptive view of an arrangement of an imaging unit and a heating unit, and a descriptive view of movement of them relative to the detection object, in the crack detection system according to the third embodiment of the present invention.

The crack detection system according to the first embodiment of the present invention has been described as being configured that the detection of a crack can be achieved by using sequentially the imaging unit 10 and the heating unit 20, which are independent from each other. The present invention is not limited only to such an embodiment, and there may be applied another embodiment as the third embodiment of the present invention, in which an imaging unit 15 and a heating unit 25 are combined together into a united body so as to provide in use a single integrated device, which is movable relative to the detection object 50, as shown in FIG. 8.

In this case, the detection of a crack can be achieved while, sequentially shifting the respective part 51 to be detected of the detection object 50, i.e., the part whose image is to be taken by the imaging device 15 and to which part heat is applied. For example, if members for tracks 60 are placed along the part 51 to be detected, which is continuously or intermittently set in the detection object, so that the device 2 in combination of the imaging unit 15 and the heating unit 25 is movable on these tracks 60 (see FIG. 8(B)), it is possible to maintain a proper positional relationship the imaging unit 15 and the heating unit 25 relative to the respective part 51 to be detected. Accordingly, it is possible not only to detect the crack in a predetermined single part to be detected, in the same manner as the first embodiment of the present invention, but also to perform repeatedly the similar detection, while moving the device 2 in combination of the imaging device and the heating device 25 to shift the part to be detected.

Thus, once the shooting range by the imaging unit 15 and the heating range by the heating unit 25 are adjusted and set finally, a mere movement of these units, while maintaining the relative positional relationship to the respective part 51 to be detected, without adjusting these ranges, may suffice for the subsequent detections for the part to be detected, thus permitting to achieve effectively the detection of the crack with the same degree of detection accuracy across a wide area of the part to be detected. In addition, it is possible to avoid the need to carry out repeatedly the installing operation of the imaging unit 15 and the heating unit 25 for every parts to be detected, thus improving efficiency of the detection operation.

Concerning the device 2 in combination of the imaging unit 15 and the heating unit 25, it is the most preferable to apply a configuration in which the shooting range by the imaging unit 15 and the heating range by the heating unit are coincide with each other and the heating unit 25 is not placed within the shooting range by the imaging unit 15, and for example, a configuration in which the imaging unit is placed on the upper side of the part 51 to be detected, to take the image of it, on the one hand, and the heating unit is placed on the lower side of the part to be detected, to apply the heat, on the other hand, thus making it possible to avid a need to move the imaging unit and the heating unit for detection of a crack in a single part to be detected. However, if it is difficult to apply such a configuration due to a specific structure of a part 51 to be detected of a detection object 50, or a heating mechanism of a heating unit 25 to be used, there may be applied a preferable configuration in which a heating unit 25 is placed on the side of a imaging unit to apply a heat to the part 51 to be detected, thus providing a compact device.

Figure 9:
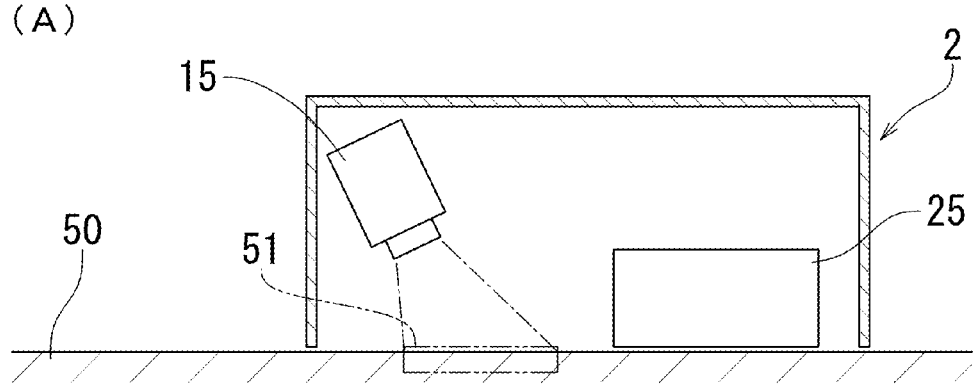
FIG. 9 is a descriptive view of steps of taking an image and applying heat in an apparatus in combination of the imaging unit and the heating unit in the crack detection system according to the third embodiment of the present invention.
Figure 9:
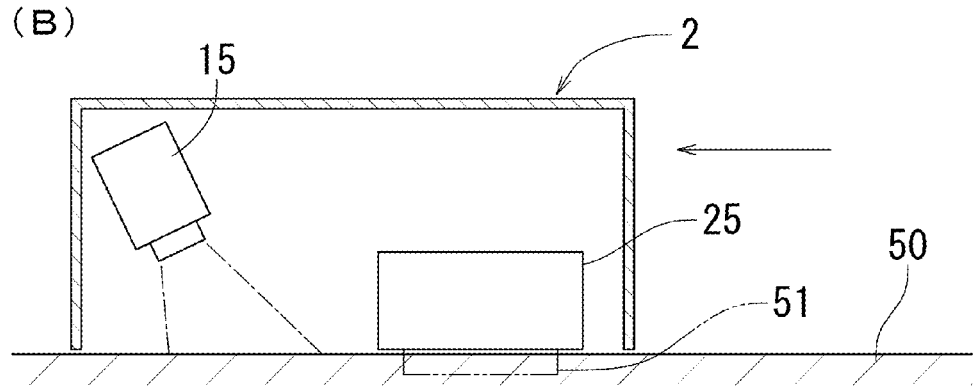
Figure 9:
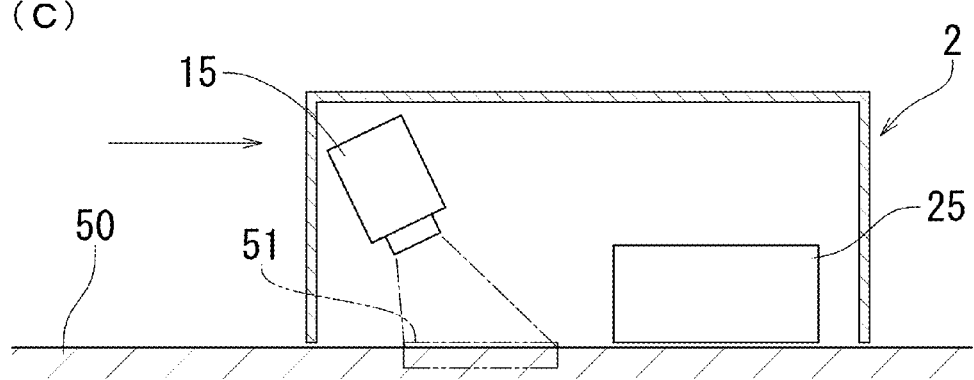

In such a configuration, in case where the imaging unit 15 is provided stationarily relative to the heating unit 25, the imaging unit 15 takes an image of the part 51 to be detected, and then the whole device is slightly moved to adjust the heating range by the heating unit 25 for the part 51 to be detected, and the heating step is carried out, and then the device 2 is returned to a position where the imaging unit has taken the image of the part 51 to be detected (see FIG. 9). In this case, the imaging unit 15 must be moved relative to the part 51 to be detected, before and after applying the heat. However, it is possible to secure the similar degree of detection accuracy to the case where the imaging unit is stationarily provided, by previously providing the detection object with a reference point for positioning the movable device to prevent misalignment of it before and after the movement, or providing the part 51 to be detected, whose image is to be taken, with a reference point, which is free of the influence of heat, for alignment of the images to carry out a matching step for the images as take before and after applying the heat.

Figure 10:
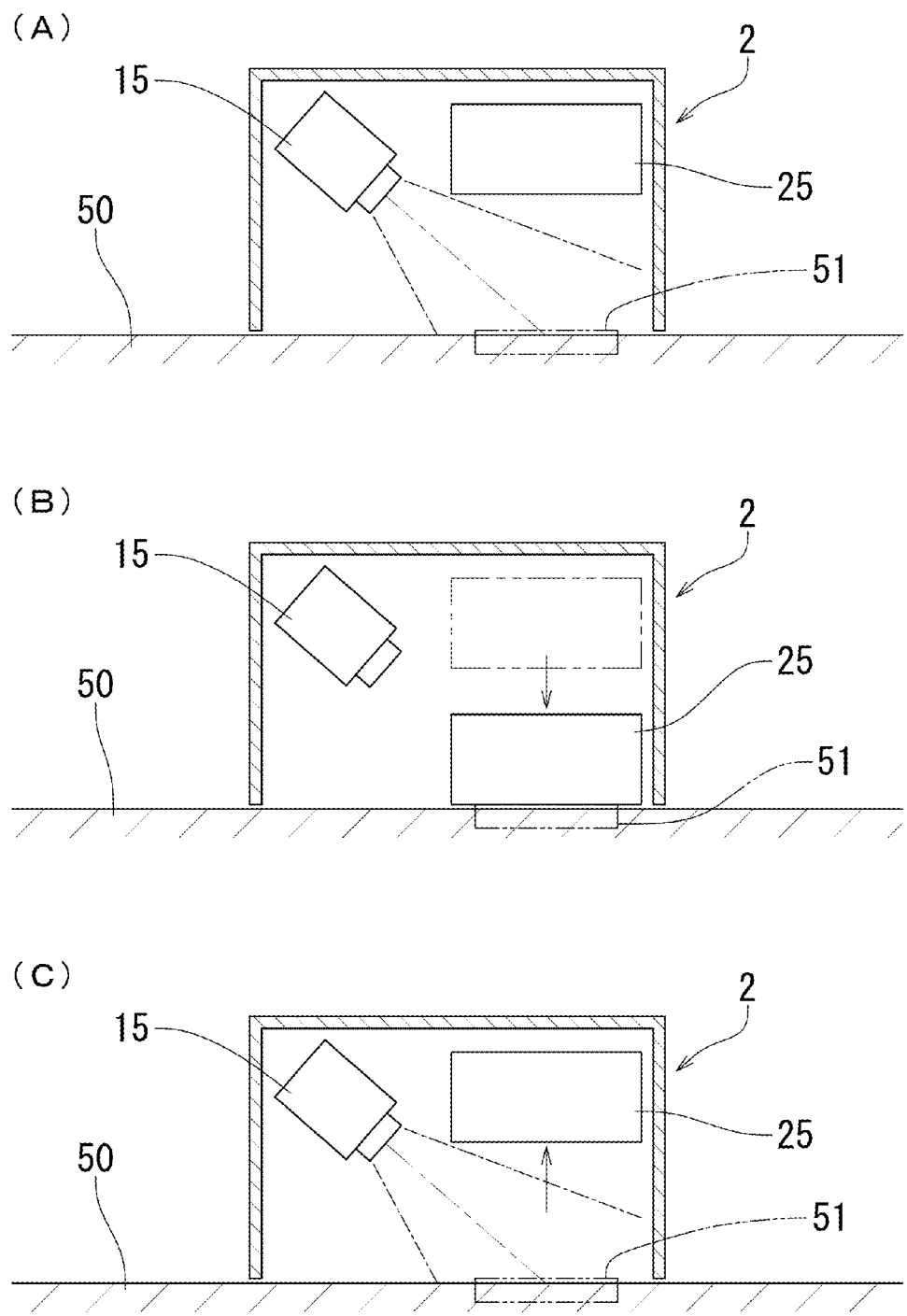
FIG. 10 is a descriptive view of steps of taking an image and applying heat in another apparatus in combination of the imaging unit and the heating unit in the crack detection system according to the third embodiment of the present invention.

To the contrary in case where the heating unit is movable relative to the imaging unit, the imaging unit 15 takes an image of the part 51 to be detected, and then the heating unit 25 is moved relative to the imaging unit 15 as stationarily provided to a position near the part to be detected, so as to permit to apply the heat to the part to be detected, and after the heating step is carried out, the heating unit 25 is moved away from the part to be detected to be returned to the original position outside the shooting range by the imaging unit 15 (see FIG. 10).

When the part 51 to be detected of the detection object 50 is placed with the upper surface facing upward, and the device in combination of the imaging unit 15 and the heating unit 25 is movable on the detection object 50 without falling from there, the device may directly travel on the detection object with no use of the tracks, etc., to continue the crack detection in the respective part to be detected. The movement of the device in combination of the imaging unit 15 and the heating unit 25 relative to the detection object 50 and the performance of taking the images and applying the heat may not be carried out manually by an operator, and such a device may be designed as an autonomous robot for an automatic operation.

When there is used a different device, which is movable along the entire surface of a structure serving as the part to be detected, for example, a cleaning device for the surface of the structure, the device in combination of the imaging unit 15 and the heating unit 25 may be connected to the above-mentioned different device to carry out the steps of taking the images and applying the heat for the crack detection, along with the movement of the different device. In this case, it is possible to avoid the mechanism of moving the device in combination of the imaging unit 15 and the heating unit 25 relative to the detection object, thus providing an effective crack detection in the respective areas of the surface of the structure in a simple structure.

The crack detection system according to each of the first to third embodiments as described above of the present invention has been described as being configured that, for the detection object 50 of the stationary structure made of steel, the strain of the respective positions of the predetermined part 51 to be detected is acquired with the use of the imaging unit and the heating unit, which are provided around the part to be detected, and the image analysis unit, and the crack is detected from the strain distribution. The present invention is not limited only to such embodiments, and there may be applied an alternative configuration that relatively small-sized industrial products moving down a production line in a factory is set as the part to be detected, a camera (cameras) provided as the imaging unit on the production line takes images of these products, a heating unit provided on the same line timely applies heat by a induction heating to the products, and an image analysis unit analyzes the images of the products as taken before and after applying the heat, to acquire the strain for detection of cracks, etc. Thus, it is possible to perform appropriately a detection of the products in a non-contact and non-destructive manner by applying the system of the present invention to a step of detecting sequentially defects in the metallic portion of the plurality of products moving down on the production line.

EXAMPLE

A test piece with a crack was actually subjected to a crack detection utilizing the crack detection system of the present invention, and there was specifically assessed whether or not detection results were influenced by difference in heating conditions.

For the crack detection system of the present invention, there were used a CCD camera serving as the imaging unit, an induction heating device serving as the heating unit, and a personal computer, which executes a program of the digital image correlation method and serves as the image analysis unit. In addition, there were supplementarily used a tripod for supporting the camera, an illuminating device for taking images, etc. A pair of CCD cameras serving as the imaging unit was used in order to achieve a three-dimensional measurement. This CCD camera has a resolution of 5,000,000 pixels each having 8-bit grayscale values. A commercially available IH cooking heater having an output of 1,000 W was used as the induction heating device serving as the heating unit. In order to make a comparison of difference in the detected results due to difference in heating method, a silicone rubber heater was used as a different type of heating unit, and a cold spray and liquid nitrogen were used as a different type of device to provide variation in temperature.

A test piece made of steel, which had been repeatedly loaded to form fine fatigue cracks, was used as the detection object for detection of a crack.

A test by a magnaflux method has previously been carried out and a width of the crack was measured by a micro loupe, in order to confirm the position of the fatigue crack in the test piece. A length of the surface crack was 155 mm, and it was confirmed that the crack actually occurred. After completion of this test, the test piece was coated with a coating layer in the same manner as the actual steel structure by applying a coating composition to the respective areas of the surface including a crack-bearing part serving as the part to be detected.

First, there was made a comparison between an example (Example No. 1 of the present invention) in which the detection was carried out with the use of the IH heater serving as the heating unit, and two examples (Comparative Example Nos. 1 and 2), and there was assessed the difference in heating conditions. In order to confirm the surface temperature of the test piece, a temperature distribution was measured through a thermography measurement.

Figure 11:
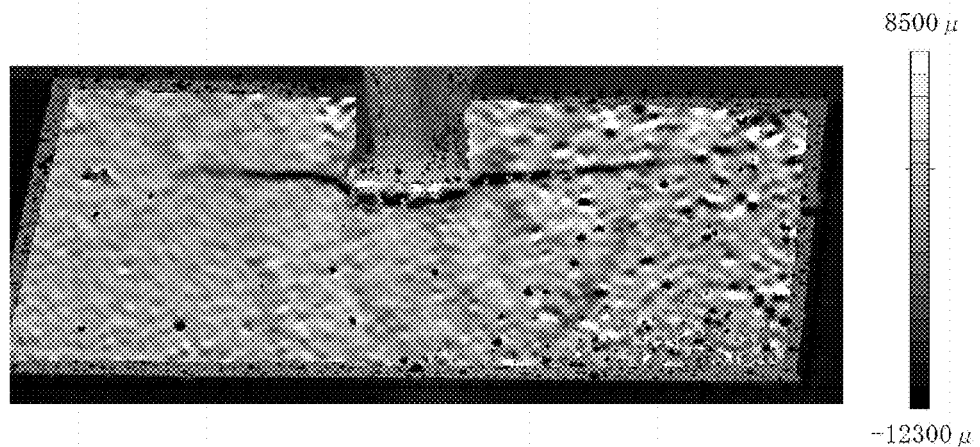
FIG. 11 is a descriptive view of a strain distribution image of a part to be detected, as obtained by the crack detection system according to Example No. 1 of the present invention.
Figure 12:
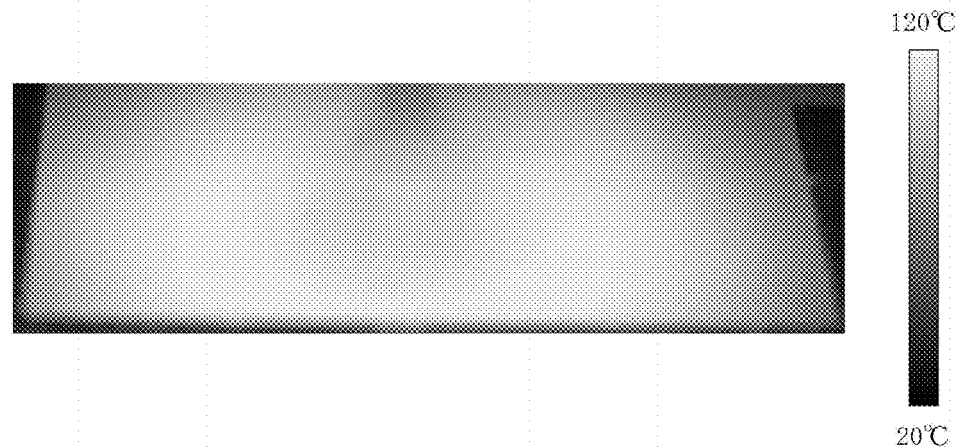
FIG. 12 is a descriptive view of a temperature distribution image of a part to be detected, as heated by the crack detection system according to Example No. 1 of the present invention.
Figure 13:
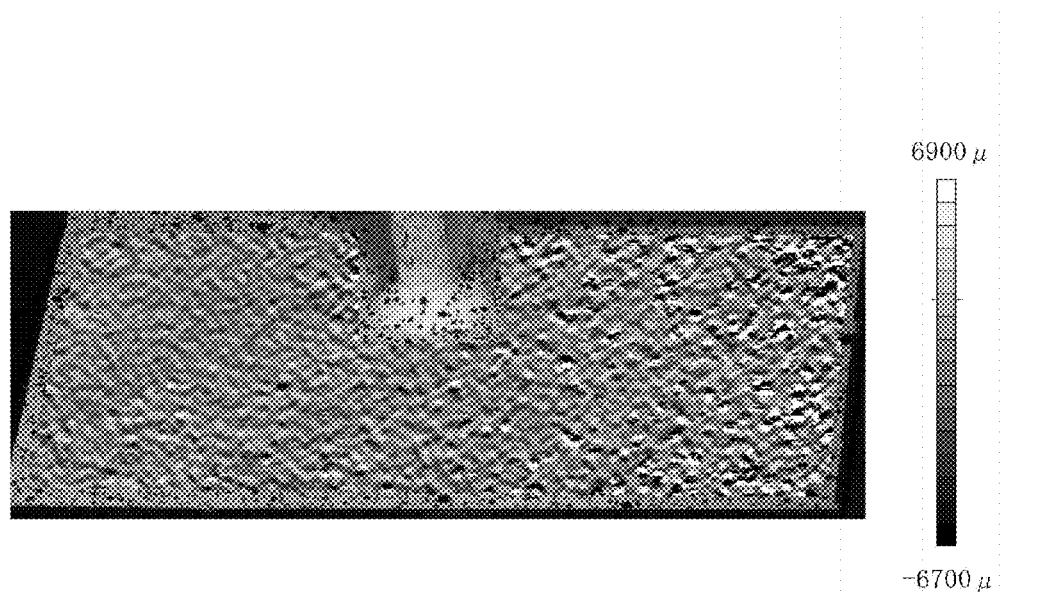
FIG. 13 is a descriptive view of a strain distribution image of a part to be detected, as obtained by a crack detection system according to Comparative Example No. 1 relative to the example of the present invention.
Figure 14:
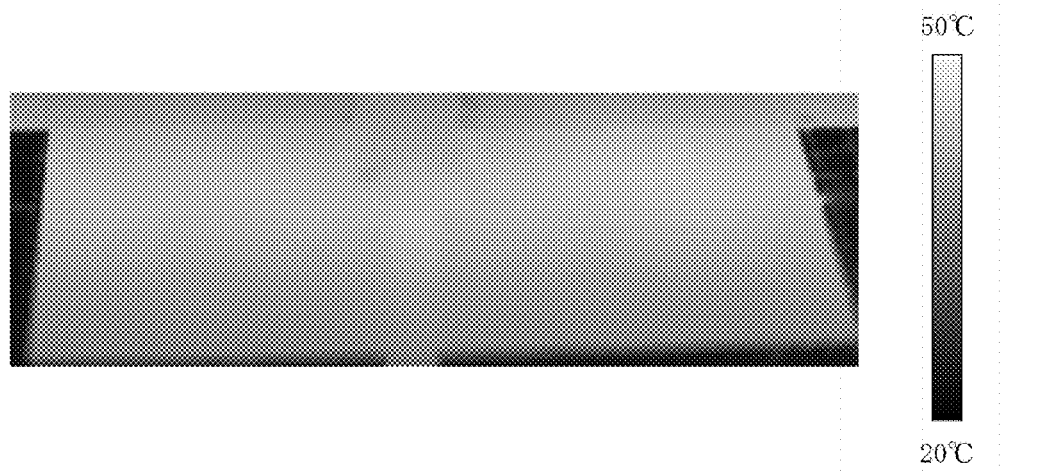
FIG. 14 is a descriptive view of a temperature distribution image of a part to be detected, as heated by the crack detection system according to Comparative Example No. 1 relative to the example of the present invention.
Figure 15:
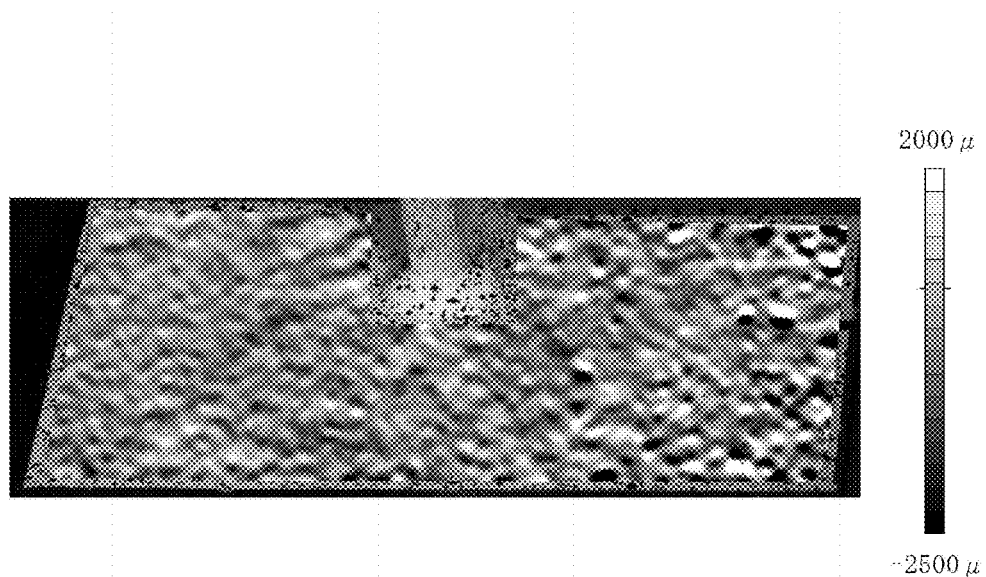
FIG. 15 is a descriptive view of a strain distribution image of a part to be detected, as obtained by the crack detection system according to Comparative Example No. 2 relative to the example of the present invention.
Figure 16:
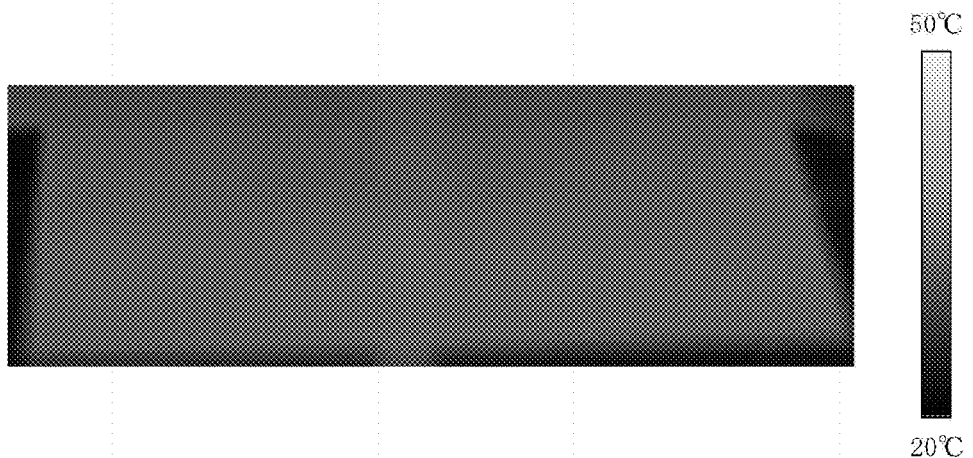
FIG. 16 is a descriptive view of a temperature distribution image of a part to be detected, as heated by the crack detection system according to Comparative Example No. 2 relative to the example of the present invention.

The distribution charts acquired by the analysis for Example No. 1 of the present invention and Comparative Example Nos. 1 and 2 are shown in FIG. 11, FIG. 13 and FIG. 15. The temperature distribution charts obtained by thermography measurement are shown in FIG. 12, FIG. 14 and FIG. 16.

It is understood from the strain distribution that, in a case of Example No. 1 of the present invention in which the heat was applied from just below the crack by the IH heater, the crack could clearly be detected. Here, the crack width, which could be detected, was 0.02 mm. The heating time by the IH heater was 5 minutes during which there was observed increase in temperature by 95° C. between about 25° C. and about 120° C.

In the strain distribution chart in Example No. 1 of the present invention, the stress appearing just above the crack is negative stress, i.e., a compression stress. The reason for this is considered that the surface (the lower surface) of the test piece on the opposite side to the surface having the crack was specifically heated by the induction heating through the IH heater provided just below the crack (the lower side of the test piece) to cause difference in temperature in the thickness direction of the test piece, with the result that there occurred a warpage in a direction in which the surface (the lower surface) of the test piece extended due to a different degree of thermal deformation at the respective position in the thickness direction of the test piece, and the surface having the crack contracted relatively to close the crack on the surface, thus causing the compression stress.

To the contrary, in Comparative Example No. 1 utilizing the rubber heater, increase in temperature by only 20° C. between about 25° C. and about 45° C. could be provided, even after applying the heat from just below the crack for 25 minutes, and the position of the crack could not be confirmed from the strain distribution chart.

In Comparative Example No. 2, the rubber heater was placed in the vicinity of the crack on the surface of the steel material to apply the heat for 10 minutes. However, it is understood from the strain distribution that the crack could not be detected in the same manner as the above-mentioned Comparative Example No. 1.

It is understood from the foregoing that in the method of heating the steel material through the heat transfer from the surface as in the rubber heater, mush time is required for the heating step and the coating layer on the surface of the steel material thermally expands during this heating step, thus making it difficult to capture the strain especially around the crack. To the contrary, in the heating method by the electromagnetic induction, only the steel material is heated without heating the coating film, thus making the strain around the crack clear.

It is clear from the foregoing that the heating step by the electromagnetic induction for even short period of time, for example 5 minutes, permits to increase sufficiently the temperature of the part to be detected. If the heating period of time is set as 5 minutes, it is possible to complete a series of steps for detection of the crack within 15 minutes at the shortest including the above-indicated heating period of time, and detect the crack in an extremely short period of time in comparison a case where the conventional common crack detection method is used, thus remarkably reducing the operating time to detect the crack and improving efficiency of detection operation.

Then, the IH heater was used as the heating unit, a position where this IH heater was to be placed was set as the right-hand and upper side of the crack on the surface of the test piece, the detection was carried out for three kinds of heating period of time (Example Nos. 2, 3 and 4 of the present invention) and there was assessed the difference in heating conditions. The heating period of time in Example No. 2 of the present invention was 15 seconds, the heating period of time in Example No. 3 of the present invention was 30 seconds and the heating period of time in Example No. 4 of the present invention was 60 seconds. In order to confirm the surface temperature of the test piece, a temperature distribution was measured through a thermography measurement.

Figure 17:
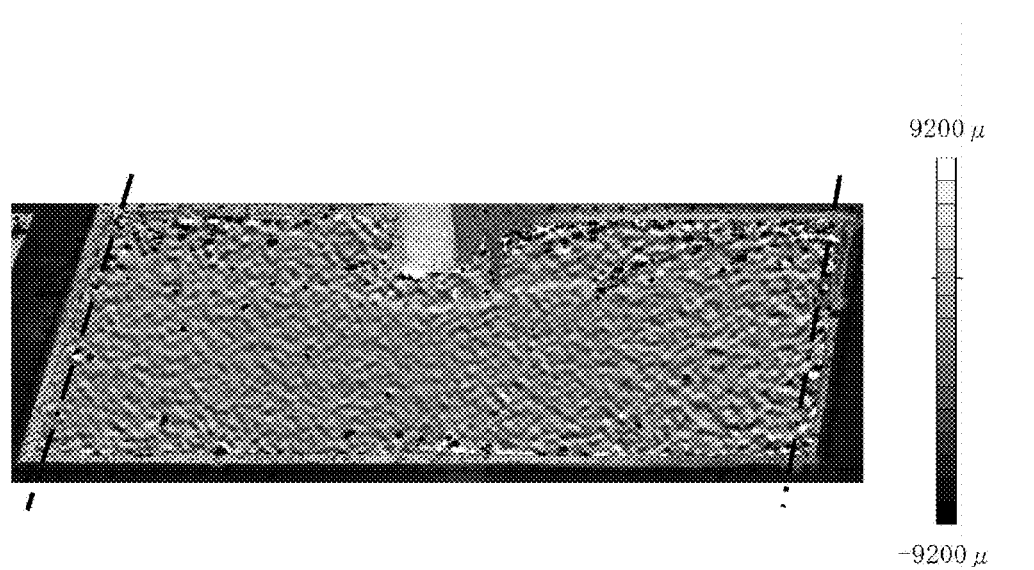
FIG. 17 is a descriptive view of a strain distribution image of a part to be detected, as obtained by the crack detection system according to Example No. 2 of the present invention.
Figure 18:
FIG. 18 is a descriptive view of a temperature distribution image of a part to be detected, as heated by the crack detection system according to Example No. 2 of the present invention.
Figure 19:
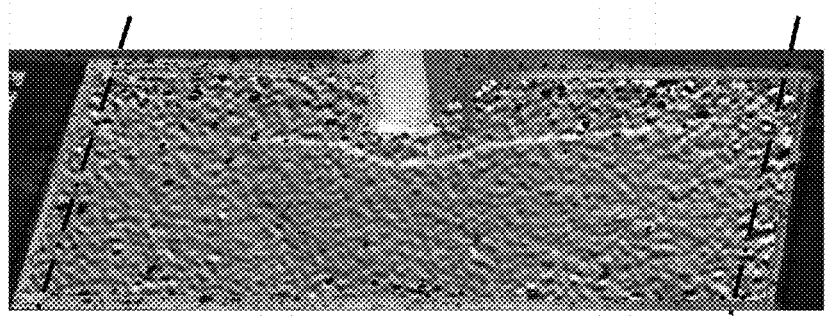
FIG. 19 is a descriptive view of a strain distribution image of a part to be detected, as obtained by the crack detection system according to Example No. 3 of the present invention.
Figure 20:
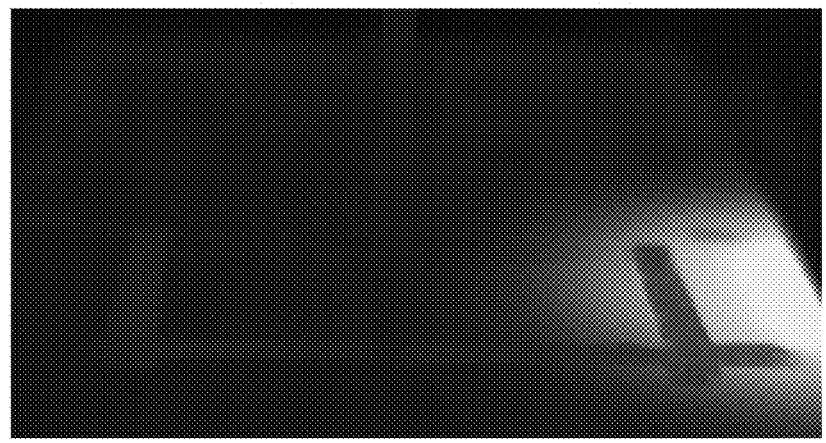
FIG. 20 is a descriptive view of a temperature distribution image of a part to be detected, as heated by the crack detection system according to Example No. 3 of the present invention.
Figure 21:
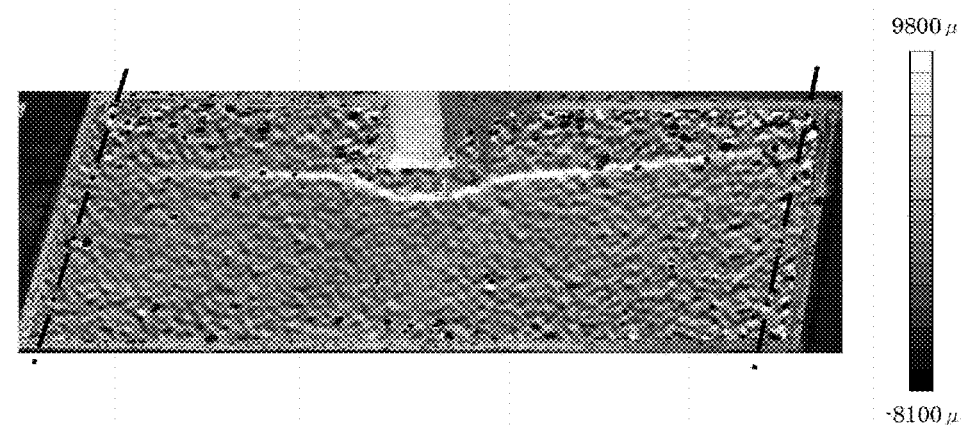
FIG. 21 is a descriptive view of a strain distribution image of a part to be detected, as obtained by the crack detection system according to Example No. 4 of the present invention.
Figure 22:
FIG. 22 is a descriptive view of a temperature distribution image of a part to be detected, as heated by the crack detection system according to Example No. 4 of the present invention.
Figure 23:
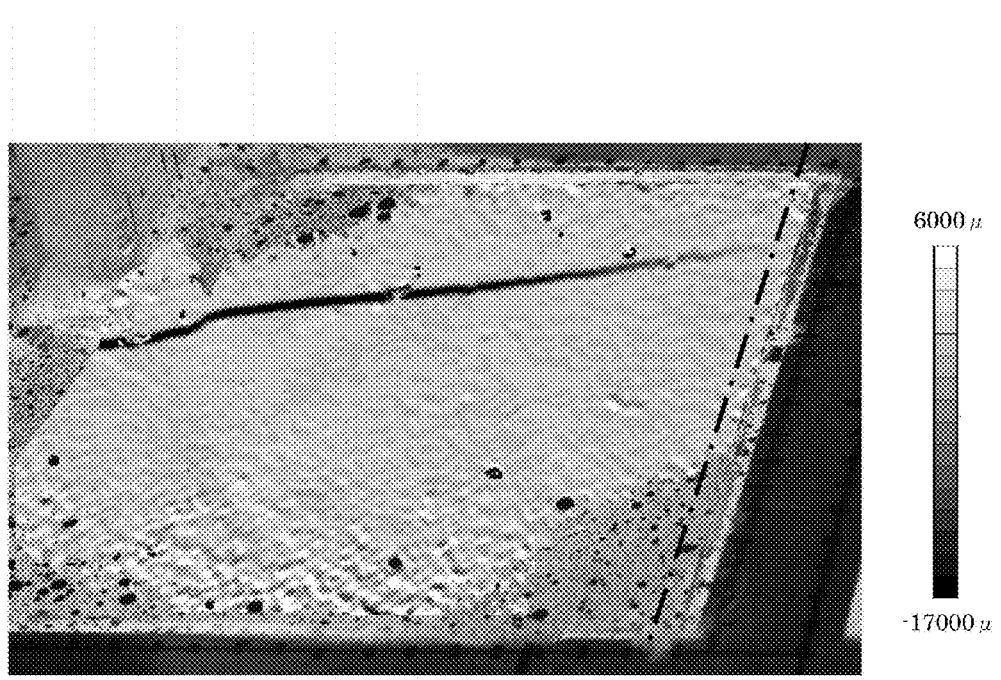
FIG. 23 is a descriptive view of a strain distribution image of a part to be detected, as obtained by the crack detection system according to Example No. 5 of the present invention.
Figure 24:
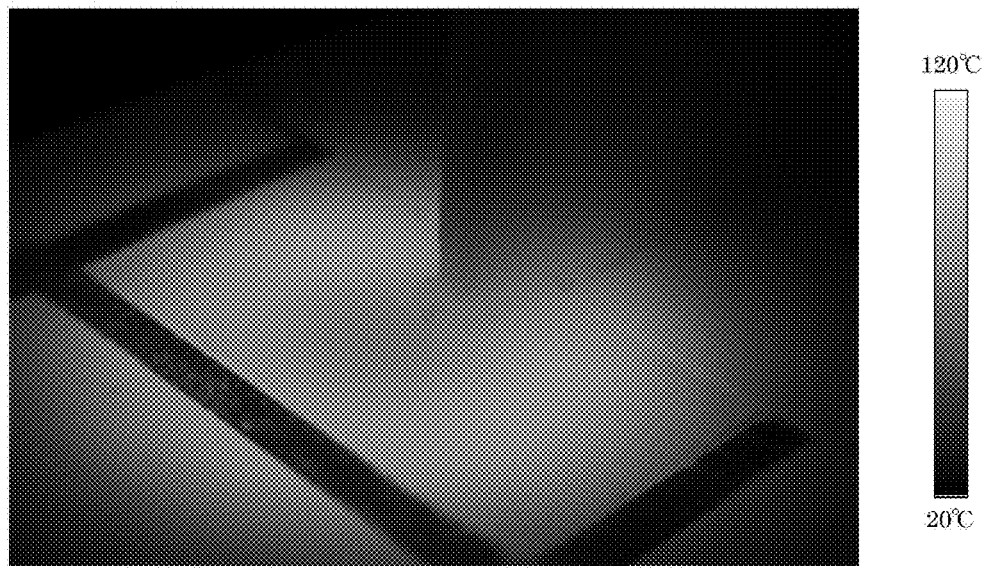
FIG. 24 is a descriptive view of a temperature distribution image of a part to be detected, as heated by the crack detection system according to Example No. 5 of the present invention.
Figure 25:
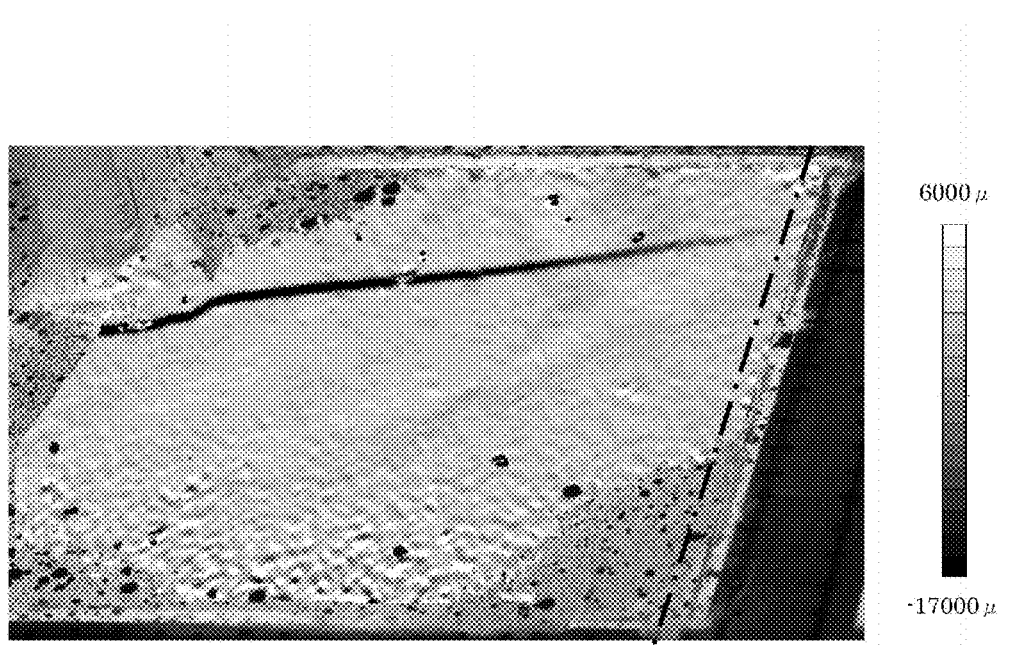
FIG. 25 is a descriptive view of a strain distribution image of a part to be detected, as obtained by the crack detection system according to Example No. 6 of the present invention.
Figure 26:
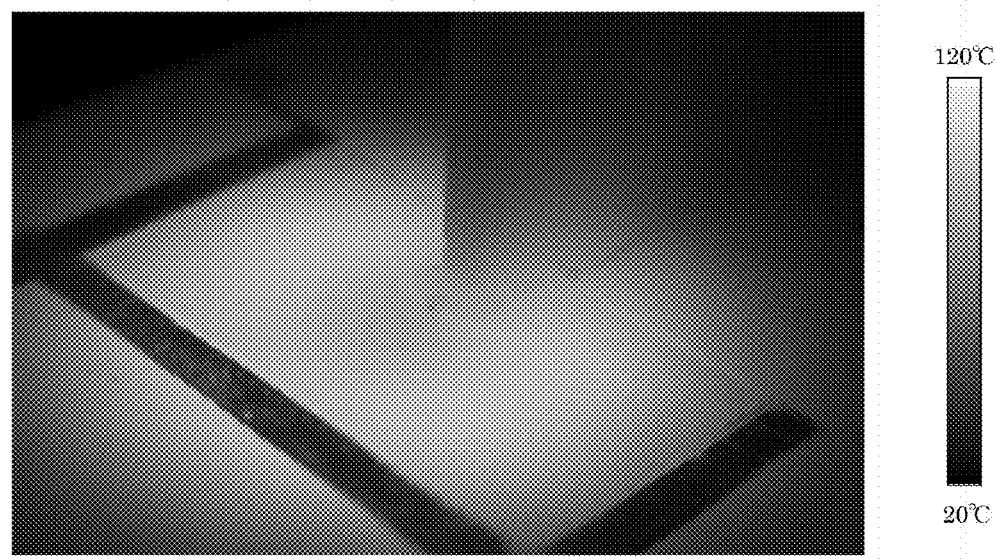
FIG. 26 is a descriptive view of a temperature distribution image of a part to be detected, as heated by the crack detection system according to Example No. 6 of the present invention.
Figure 27:
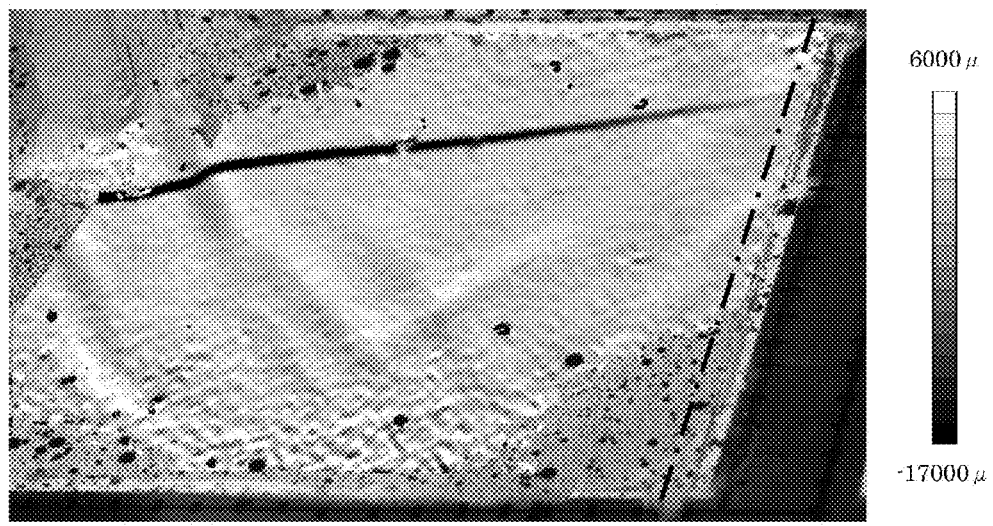
FIG. 27 is a descriptive view of a strain distribution image of a part to be detected, as obtained by the crack detection system according to Example No. 7 of the present invention.
Figure 28:
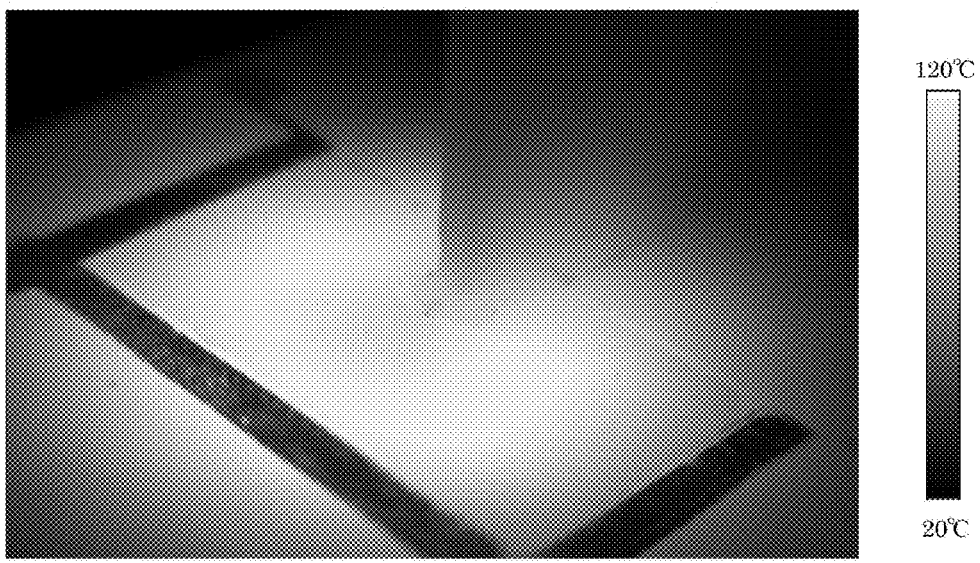
FIG. 28 is a descriptive view of a temperature distribution image of a part to be detected, as heated by the crack detection system according to Example No. 7 of the present invention.
Figure 29:
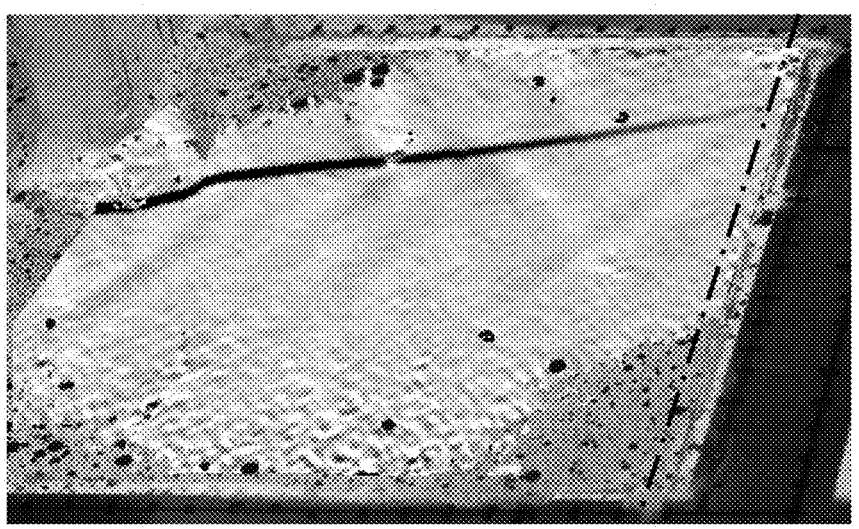
FIG. 29 is a descriptive view of a strain distribution image of a part to be detected, as obtained by the crack detection system according to Example No. 8 of the present invention.
Figure 30:
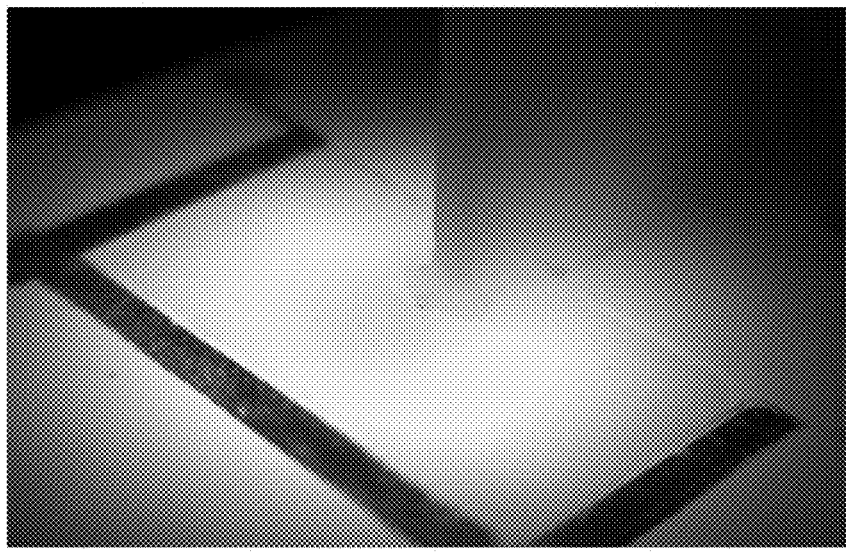
FIG. 30 is a descriptive view of a temperature distribution image of a part to be detected, as heated by the crack detection system according to Example No. 8 of the present invention.
Figure 31:
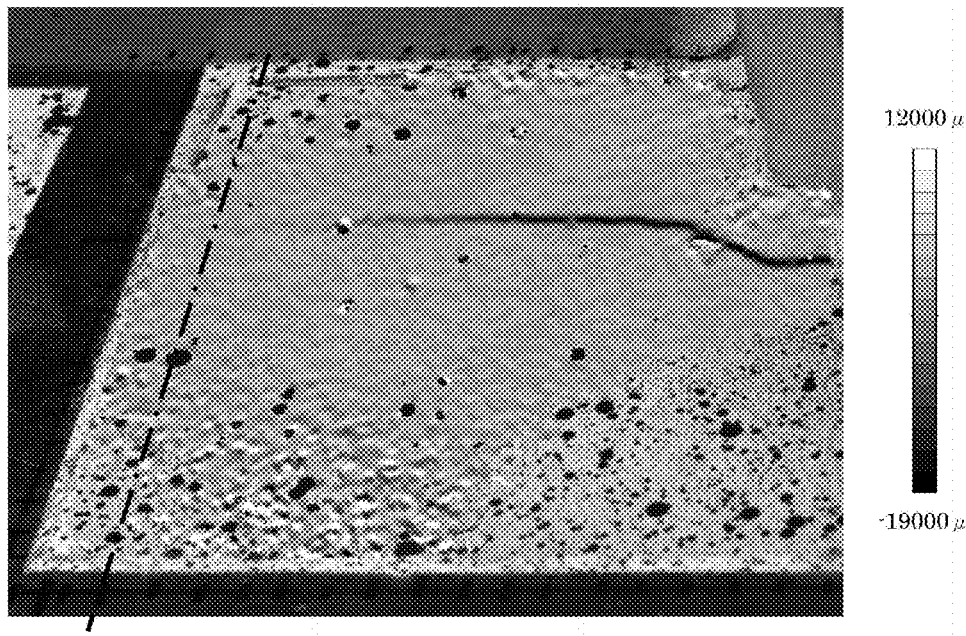
FIG. 31 is a descriptive view of a strain distribution image of a part to be detected, as obtained by the crack detection system according to Example No. 9 of the present invention.
Figure 32:
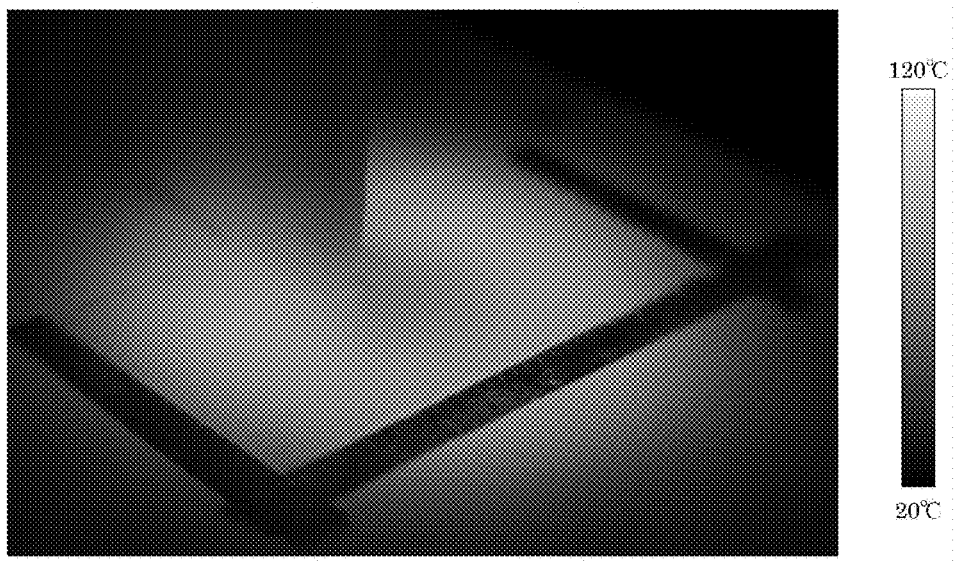
FIG. 32 is a descriptive view of a temperature distribution image of a part to be detected, as heated by the crack detection system according to Example No. 9 of the present invention.
Figure 33:
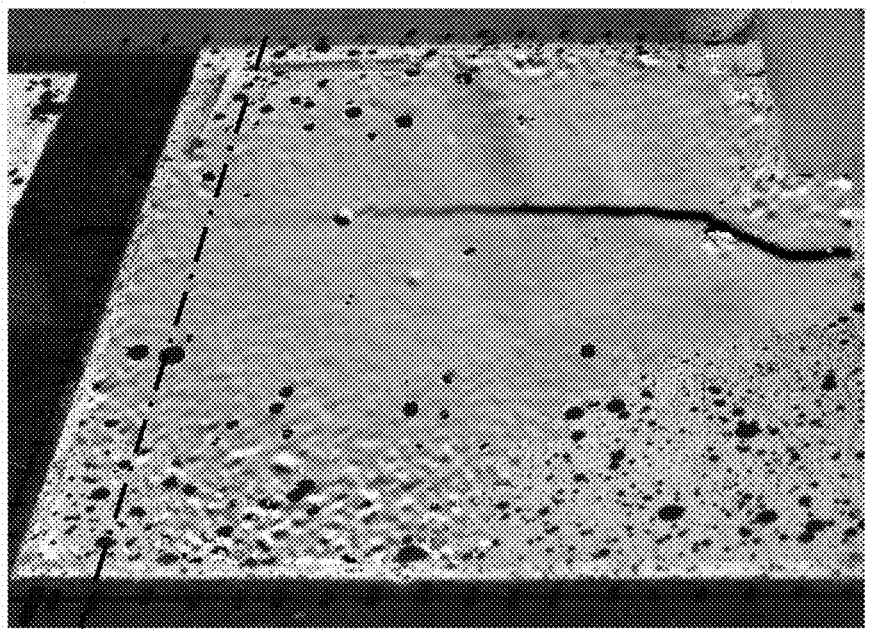
FIG. 33 is a descriptive view of a strain distribution image of a part to be detected, as obtained by the crack detection system according to Example No. 10 of the present invention.
Figure 34:
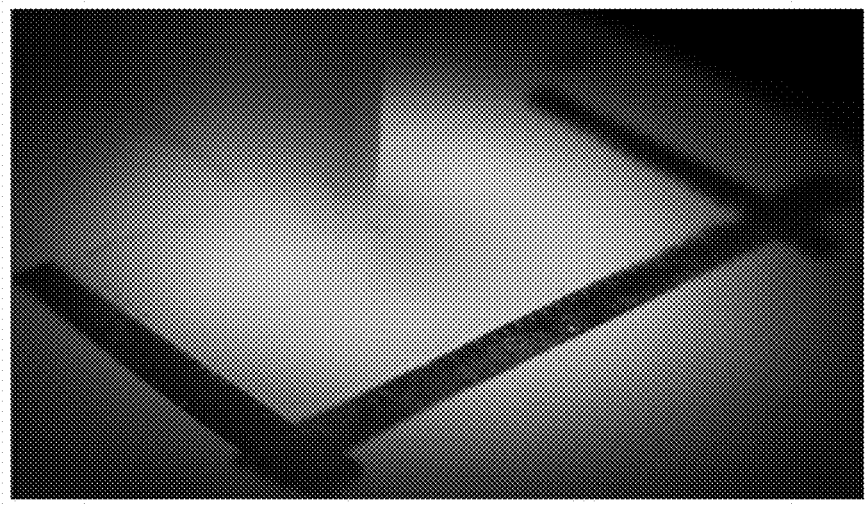
FIG. 34 is a descriptive view of a temperature distribution image of a part to be detected, as heated by the crack detection system according to Example No. 10 of the present invention.
Figure 35:
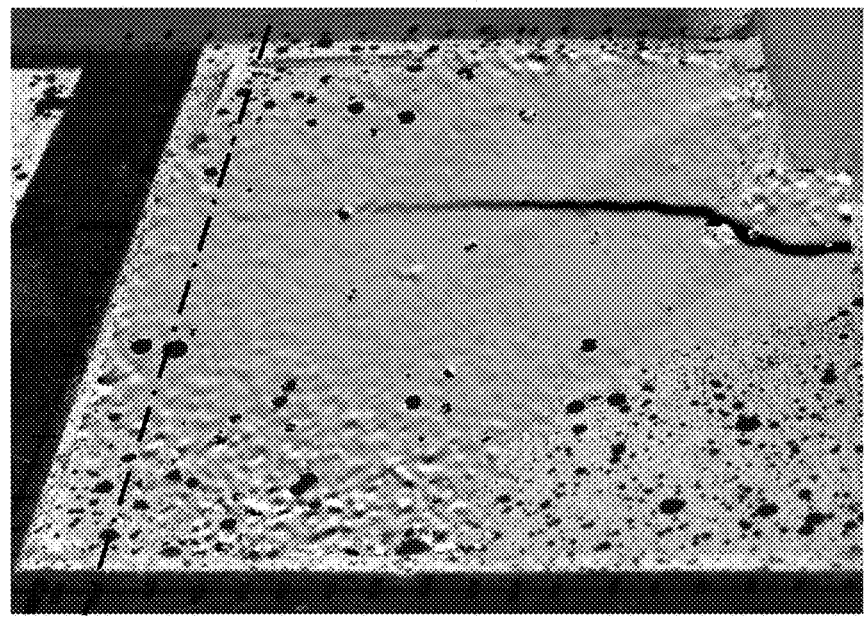
FIG. 35 is a descriptive view of a strain distribution image of a part to be detected, as obtained by the crack detection system according to Example No. 11 of the present invention.
Figure 36:
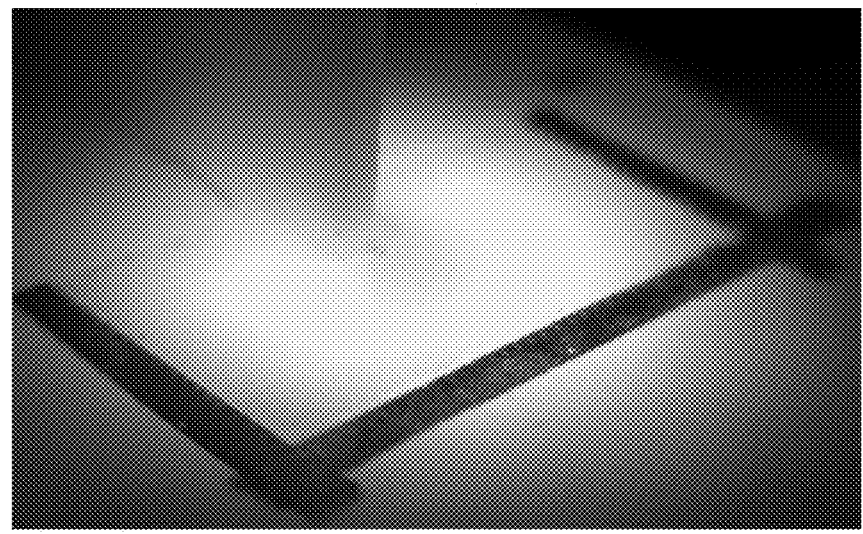
FIG. 36 is a descriptive view of a temperature distribution image of a part to be detected, as heated by the crack detection system according to Example No. 11 of the present invention.
Figure 37:
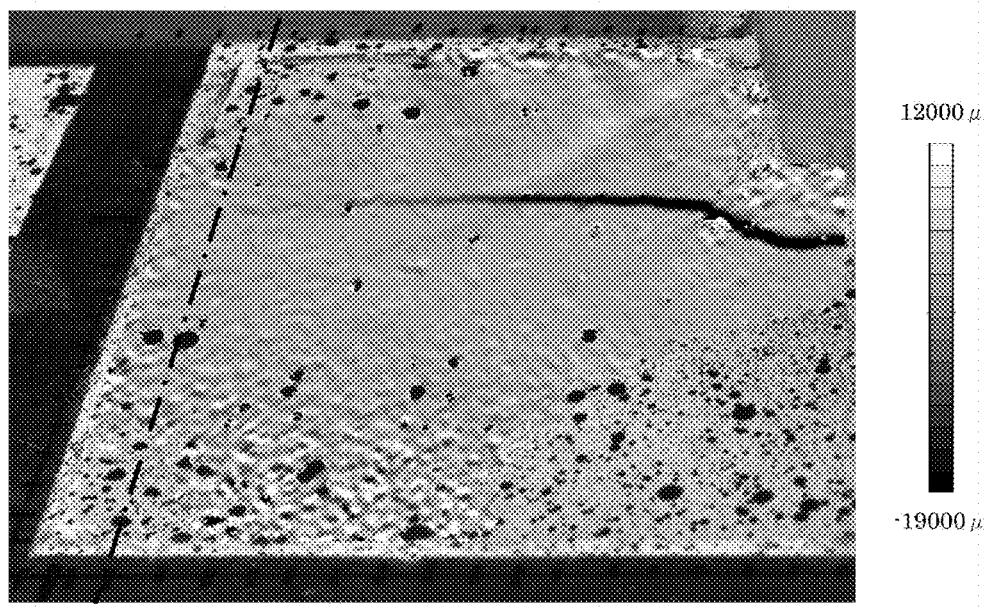
FIG. 37 is a descriptive view of a strain distribution image of a part to be detected, as obtained by the crack detection system according to Example No. 12 of the present invention.
Figure 38:
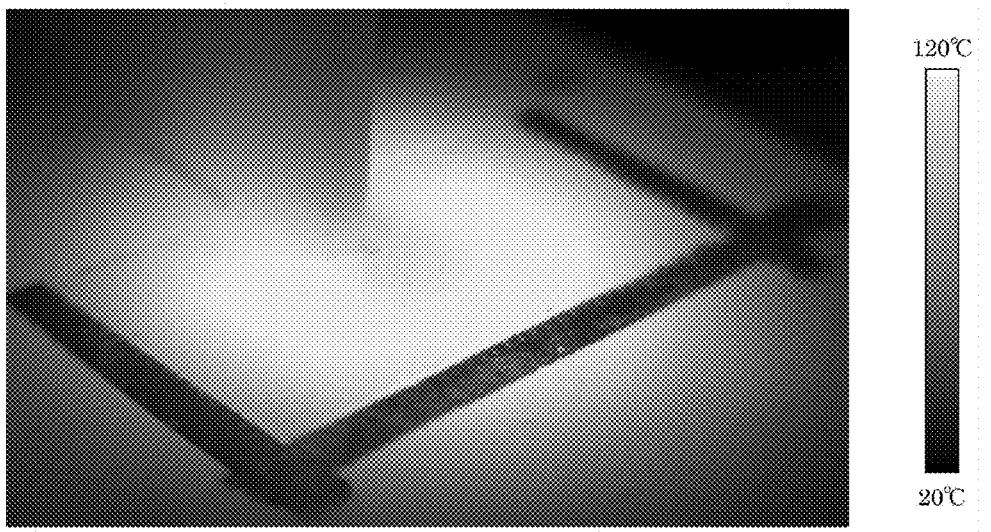
FIG. 38 is a descriptive view of a temperature distribution image of a part to be detected, as heated by the crack detection system according to Example No. 12 of the present invention.

The distribution charts acquired by the analysis for Example Nos. 2, 3 and 4 of the present invention are shown in FIG. 17, FIG. 19 and FIG. 21. In the distribution chart, a pair of dashed-dotted lines indicates positions of both ends of the crack. The temperature distribution charts obtained by thermography measurement are shown in FIG. 18, FIG. 20 and FIG. 22, respectively.

In Example No. 2 of the present invention (the heating period of time of 15 seconds), the existence of the crack could be confirmed in an area, which indicated a large width of the crack, in the central portion of the test piece. In Example No. 3 of the present invention (the heating period of time of 30 seconds), the crack could be detected almost entire area of the test piece. In Example No. 4 of the present invention (the heating period of time of 60 seconds), the strain could be confirmed along the crack across it, thus permitting to detect the crack.

In Example Nos. 2, 3 and 4 of the present invention, the IH heater was placed on the one side of the test piece having the crack, but a remarkable variation of strain appeared around the crack on the opposite side where the IH heater was not placed. The reason for this is considered that the surface (the lower surface) of the test piece having the crack just below the IH heater was specifically heated by the induction heating to cause difference in temperature in the thickness direction of the test piece, with the result that there occurred a warpage in a direction in which the surface of the test piece extended, due to a different degree of thermal deformation at the respective position in the thickness direction of the test piece, and the crack on the surface as heated opened, thus causing such a remarkable variation of strain. In addition, it is considered that the influence by the warpage also affected the opposite side of the test piece, where the IH heater was not provided, and the crack opened in the similar manner, thus causing such a remarkable variation of strain.

Then, the IH heater was used as the heating unit, a position where this IH heater was to be placed as set as just below the crack on the lower surface of the test piece, the detection was carried out for the test piece in which the range to be detected (the shooting range) has been set as the area between the central portion of the test piece and the right side portion of it, when the surface temperature of the test piece reached the predetermined temperature stage (about 80° C., about 100° C., about 120° C. and about 150° C.) during the heating step with the heating period of time of 275 seconds, and there was assessed the variation in the strain distribution along with the progress of the heating (Example Nos. 5, 6, 7 and 8 of the present invention). The surface temperatures at the time when carrying out the detection for the respective examples of the present invention were about 80° C. in Example No. 5 of the present invention, about 100° C. in Example No. 6 of the present invention, about 120° C. in Example No. 7 of the present invention and about 150° C. in Example No. 8 of the present invention. In order to confirm the surface temperature of the test piece, a temperature distribution was measured through a thermography measurement in the same manner as the examples as described above of the present invention.

Under the same conditions as described above, the detection was also carried out for the test piece in which the range to be detected (the shooting range) has been set as the area between the central portion of the test piece and the left side portion of it, at the above-mentioned four temperature stages of the surface temperature of the test piece, and there was assessed the variation in the strain distribution along with the progress of the heating (Example Nos. 9, 10, 11 and 12 of the present invention). The surface temperatures at the time when carrying out the detection for the respective examples of the present invention were about 80° C. in Example No. 9 of the present invention, about 100° C. in Example No. 10 of the present invention, about 120° C. in Example No. 11 of the present invention and about 150° C. in Example No. 12 of the present invention.

The strain distributions as acquired by the analysis at the respective temperature stages in Examples Nos. 5, 6, 7 and 8 of the present invention as well as Example Nos. 9, 10, 11 and 12 of the present invention are shown in FIG. 23, FIG. 25, FIG. 27, FIG. 29, FIG. FIG. 31, FIG. 33, FIG. 35 and FIG. 37, respectively. In the strain distribution in FIG. 23, FIG. 25, FIG. 27 and FIG. 29, a dashed-dotted line on the right-hand side indicates a position of the right-hand end of the crack, and in the strain distribution in FIG. 31, FIG. 33, FIG. 35 and FIG. 37, a dashed-dotted line on the left-hand side indicates a position of the left-hand end of the crack. The temperature distribution charts as obtained by thermography measurement are shown in FIG. 24, FIG. 26, FIG. 28, FIG. 30, FIG. 32, FIG. 34, FIG. 36 and FIG. 38.

It is understood from the strain distributions in Example Nos. 5 and 9 of the present invention that even the edge of the crack can be detected even at the surface temperature of the test piece of 80° C. In this case, the stress appearing just above the crack is a compression stress. The reason for this is considered that the surface (the lower surface) of the test piece on the opposite side to the surface having the crack was specifically heated by the induction heating through the IH heater provided just below the lower side of the test piece to cause difference in temperature in the thickness direction of the test piece, with the result that there occurred a warpage in a direction in which the surface (the lower surface) of the test piece extended due to a different degree of thermal deformation at the respective position in the thickness direction of the test piece, and the surface having the crack contracted relatively to close the crack on the surface, thus causing the compression stress.

In addition, for the comparative examples, there was assessed whether or not the crack could be detected in the two examples in which a cooling device was used in place of the heating unit, and an attempt to detect the crack was made after cooling the test piece having a room temperature from its surface (Comparative Example Nos. 3 and 4). A cold spray was used as the cooling device in Comparative Example No. 3, and liquid nitrogen was used in Comparative Example No. 4. In order to confirm the surface temperature of the test piece also in these comparative examples, a temperature distribution was measured through a thermography measurement.

Figure 39:
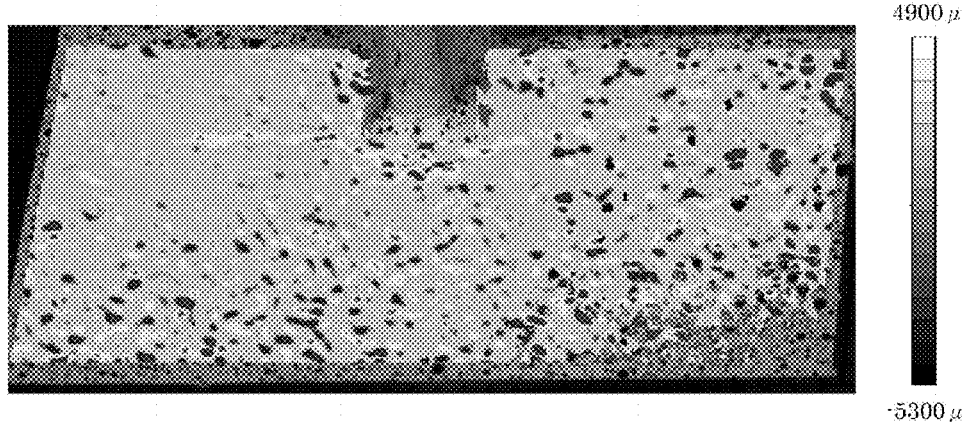
FIG. 39 is a descriptive view of a strain distribution image of a part to be detected, as obtained by the crack detection system according to Comparative Example No. 3 relative to the example of the present invention.
Figure 40:
FIG. 40 is a descriptive view of a temperature distribution image of a part to be detected, as heated by the crack detection system according to Comparative Example No. 3 relative to the example of the present invention.
Figure 41:
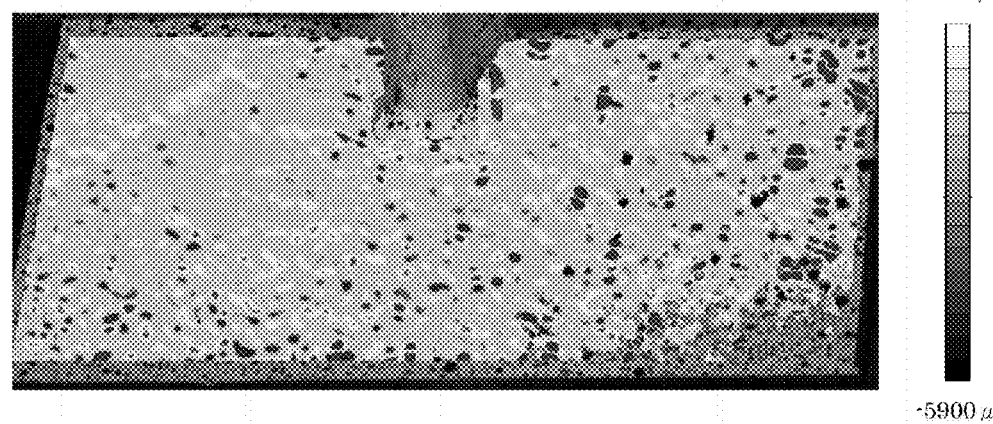
FIG. 41 is a descriptive view of a strain distribution image of a part to be detected, as obtained by the crack detection system according to Comparative Example No. 4 relative to the example of the present invention.
Figure 42:
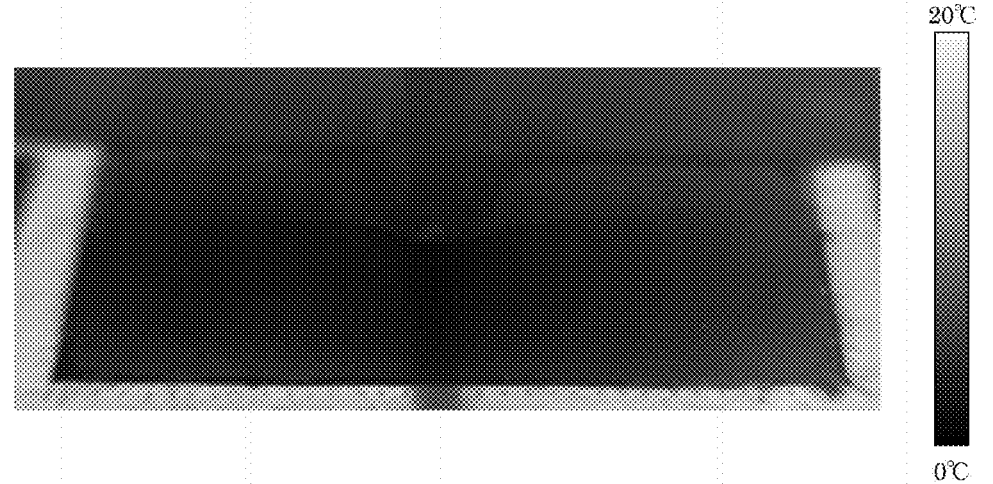
FIG. 42 is a descriptive view of a temperature distribution image of a part to be detected, as heated by the crack detection system according to Comparative Example No. 4 relative to the example of the present invention.

The distribution charts acquired by the analysis for Comparative Example Nos. 3 and 4 are shown in FIG. 39 and FIG. 41, respectively. The temperature distribution charts obtained by thermography measurement are shown in FIG. 40 and FIG. 42.

In each of the cases of Comparative Example No. 3 in which the test piece was cooled from its surface by the cold spray and of Comparative Example No. 4 in which the test piece was cooled from its surface by the liquid nitrogen, it was not possible to clearly confirm the position of the crack from the strain distribution. It is understood that the heat transfer from the surface of the test piece could not cause a temperature variation only at the steel portion, in the same manner as the above-described case where the test piece was heated by the rubber heater, the strain around the crack of the steel portion could not be captured due to influence of deformation of the coating layer on the surface of the steel portion.

As is clear from the foregoing, there is a clear difference in distinguishability of the crack from the strain distribution, between the case where the IH heater serving as the heating unit is used to cause a temperature variation directly on the steel portion of the test piece and the other case where the temperature variation is caused by the heat transfer from the surface of the test piece in the comparative example. Especially, the use of the IH heater enables the crack to be detected even at the temperature of 80° C., which gives almost no influence to the coating layer. When there is applied the crack detection system according to the present invention in which the part to be detected is heated by the induction heating and the images of the coating layer of the surface of the part to be detected are taken before and after applying the heat, and the resultant images as taken before and after applying the heat are analyzed through a digital image correlation method to acquire the strain distribution in the part to be detected, it is possible to detect the crack in the part to be detected in a short period of detecting time including a short period of heating time, while maintaining the protection of the part to be detected, by the coating layer, without any adverse influence on the coating layer.

REFERENCE SIGNS LIST

| | |
|---|---|
| 1 | crack detection system |
| 10, 15 | imaging unit |
| 20, 25 | heating unit |
| 22 | heating unit |
| 23 | heating coil |
| 30 | image analysis unit |
| 40 | display unit |
| 50 | detection object |
| 51 | part to be detected |
| 52 | steel material |
| 53 | coating layer |
| 54 | crack |
| 60 | track |

What is claimed is:

1. A crack detection system, which comprises:
an imaging unit that takes an image of an outermost coating surface of a predetermined part to be detected, of a detection object, which part comprises a main body formed of a conductive material and a coating layer formed of a non-conductive material, with which the main body is coated from outside;
a heating unit that applies heat to at least a surface area of said part to be detected, to increase a temperature of said coating layer to a predetermined temperature by which said coating layer may not degrade, by an induction heating applied to the part to be detected and/or a heat transfer in a vicinity of the part to be detected, along with the induction heating applied to the part to be detected; and
an image analysis unit that analyzes two images of the same detection object, which have been taken at different times, to determine strain between the two images in respective positions within a range for detection and acquire a strain distribution within the range for detection;
wherein:
said imaging unit takes the image of said coating surface of said part to be detected before applying the heat by means of said heating unit and immediately after applying the heat;
said image analysis unit determines the strain by the analysis from the two images of the part to be detected, which have taken by said imaging unit before and after applying the heat, in respective positions of the part to be detected, to acquire the strain distribution in the part to be detected; and
the strain distribution in the part to be detected includes, in a case where a crack exists in the part to be detected, a group of strains in which strains are concentrated almost linearly in a quite different form from other strains around the group of strains in the strain distribution, in response to a small displacement of an area with the crack due to application of the heat.

2. The crack detection system as claimed in claim 1, wherein:
said heating unit comprises a coil that generates an eddy current in the part to be detected through an electromagnetic induction to generate heat of the part to be detected; and
an alternating electric current that has a frequency, which is equal to or more than a predetermined frequency, and is capable of heating only a surface area, on a side near the heating unit, of the part to be detected, through a skin effect by the eddy current, to generate a difference in temperature in a thickness direction of the part to be detected, when applying heat, is applied to said coil to achieve the induction heating of the part to be detected.

3. The crack detection system as claimed in claim 1, further comprising:
a display unit that display the strain distribution, which has been acquired by said image analysis unit, as an image in a form of a strain distribution chart, which is associated with an image region of the part to be detected; and
wherein:
said display unit makes the group of strains in which at least the strains are concentrated almost linearly in the image of said strain distribution chart, clearly distinguishable in a displayed state from the other strains around the group of strains to display the group of strains in a visually distinguishable manner.

4. The crack detection system as claimed in claim 2, wherein:
said imaging unit comprises one or more portable cameras; and
said image analysis unit comprises a transportable computer that is capable of receiving input data of images from the camera serving as said imaging unit, and that utilizes a predetermined program to determine the strain in respective positions of the part to be detected, from the two images of the part to be detected, which have been taken by said imaging unit before and after applying the heat, by an analysis of a digital image correlation method, so as to perform a function of acquiring the strain distribution in the part to be detected.

5. The crack detection system as claimed in claim 1, wherein:
said imaging unit is placed in a predetermined position distant from the part to be detected, by a distance longer than that between the part to be detected and a position of the heating unit when performing the induction heating, so as to take the image of the part to be detected, without a relative movement of the imaging unit to the part to be detected, before and after applying the heat to the part to be detected, by means of the heating unit.

6. The crack detection system as claimed in claim 1, wherein:
said imaging unit and said heating unit are connected to each other so as to be movable in a united body relative to said part to be detected;
said heating unit is adapted to heat the part to be detected, from a side in a vicinity of the part to be detected on a side where the imaging unit is placed; and
said imaging unit and said heating unit are movable relative to the detection object so as to reach sequentially positions in which steps of taking the image and applying the heat can be performed, respectively, to carry out the steps of taking the image and applying the heat, respectively, without changing a relative positional relationship to each of the parts to be detected, which are set on a continuous flat plane or a continuous curved plane for the detection object.

7. The crack detection system as claimed in claim 2, further comprising:
a display unit that display the strain distribution, which has been acquired by said image analysis unit, as an image in a form of a strain distribution chart, which is associated with an image region of the part to be detected; and
wherein:
said display unit makes the group of strains in which at least the strains are concentrated almost linearly in the image of said strain distribution chart, clearly distinguishable in a displayed state from the other strains around the group of strains to display the group of strains in a visually distinguishable manner.

8. The crack detection system as claimed in claim 3, wherein:
said imaging unit comprises one or more portable cameras; and
said image analysis unit comprises a transportable computer that is capable of receiving input data of images from the camera serving as said imaging unit, and that utilizes a predetermined program to determine the strain in respective positions of the part to be detected, from the two images of the part to be detected, which have been taken by said imaging unit before and after applying the heat, by an analysis of a digital image correlation method, so as to perform a function of acquiring the strain distribution in the part to be detected.

9. The crack detection system as claimed in claim 7, wherein:
said imaging unit comprises one or more portable cameras; and
said image analysis unit comprises a transportable computer that is capable of receiving input data of images from the camera serving as said imaging unit, and that utilizes a predetermined program to determine the strain in respective positions of the part to be detected, from the two images of the part to be detected, which have been taken by said imaging unit before and after applying the heat, by an analysis of a digital image correlation method, so as to perform a function of acquiring the strain distribution in the part to be detected.

10. The crack detection system as claimed in claim 2, wherein:
said imaging unit is placed in a predetermined position distant from the part to be detected, by a distance longer than that between the part to be detected and a position of the heating unit when performing the induction heating, so as to take the image of the part to be detected, without a relative movement of the imaging unit to the part to be detected, before and after applying the heat to the part to be detected, by means of the heating unit.

11. The crack detection system as claimed in claim 3, wherein:
said imaging unit is placed in a predetermined position distant from the part to be detected, by a distance longer than that between the part to be detected and a position of the heating unit when performing the induction heating, so as to take the image of the part to be detected, without a relative movement of the imaging unit to the part to be detected, before and after applying the heat to the part to be detected, by means of the heating unit.

12. The crack detection system as claimed in claim 4, wherein:
said imaging unit is placed in a predetermined position distant from the part to be detected, by a distance longer than that between the part to be detected and a position of the heating unit when performing the induction heating, so as to take the image of the part to be detected, without a relative movement of the imaging unit to the part to be detected, before and after applying the heat to the part to be detected, by means of the heating unit.

13. The crack detection system as claimed in claim 7, wherein:
said imaging unit is placed in a predetermined position distant from the part to be detected, by a distance longer than that between the part to be detected and a position of the heating unit when performing the induction heating, so as to take the image of the part to be detected, without a relative movement of the imaging unit to the part to be detected, before and after applying the heat to the part to be detected, by means of the heating unit.

14. The crack detection system as claimed in claim 8, wherein:
said imaging unit is placed in a predetermined position distant from the part to be detected, by a distance longer than that between the part to be detected and a position of the heating unit when performing the induction heating, so as to take the image of the part to be detected, without a relative movement of the imaging unit to the part to be detected, before and after applying the heat to the part to be detected, by means of the heating unit.

15. The crack detection system as claimed in claim 9, wherein:
said imaging unit is placed in a predetermined position distant from the part to be detected, by a distance longer than that between the part to be detected and a position of the heating unit when performing the induction heating, so as to take the image of the part to be detected, without a relative movement of the imaging unit to the part to be detected, before and after applying the heat to the part to be detected, by means of the heating unit.

16. The crack detection system as claimed in claim 2, wherein:

said imaging unit and said heating unit are connected to each other so as to be movable in a united body relative to said part to be detected;

said heating unit is adapted to heat the part to be detected, from a side in a vicinity of the part to be detected on a side where the imaging unit is placed; and said imaging unit and said heating unit are movable relative to the detection object so as to reach sequentially positions in which steps of taking the image and applying the heat can be performed, respectively, to carry out the steps of taking the image and applying the heat, respectively, without changing a relative positional relationship to each of parts to be detected, which are set on a continuous flat plane or a continuous curved plane for the detection object.

17. The crack detection system as claimed in claim 3, wherein:

said imaging unit and said heating unit are connected to each other so as to be movable in a united body relative to said part to be detected;

said heating unit is adapted to heat the part to be detected, from a side in a vicinity of the part to be detected on a side where the imaging unit is placed; and said imaging unit and said heating unit are movable relative to the detection object so as to reach sequentially positions in which steps of taking the image and applying the heat can be performed, respectively, to carry out the steps of taking the image and applying the heat, respectively, without changing a relative positional relationship to each of parts to be detected, which are set on a continuous flat plane or a continuous curved plane for the detection object.

18. The crack detection system as claimed in claim 4, wherein:

said imaging unit and said heating unit are connected to each other so as to be movable in a united body relative to said part to be detected;

said heating unit is adapted to heat the part to be detected, from a side in a vicinity of the part to be detected on a side where the imaging unit is placed; and said imaging unit and said heating unit are movable relative to the detection object so as to reach sequentially positions in which steps of taking the image and applying the heat can be performed, respectively, to carry out the steps of taking the image and applying the heat, respectively, without changing a relative positional relationship to each of parts to be detected, which are set on a continuous flat plane or a continuous curved plane for the detection object.

19. The crack detection system as claimed in claim 7, wherein:

said imaging unit and said heating unit are connected to each other so as to be movable in a united body relative to said part to be detected;

said heating unit is adapted to heat the part to be detected, from a side in a vicinity of the part to be detected on a side where the imaging unit is placed; and said imaging unit and said heating unit are movable relative to the detection object so as to reach sequentially positions in which steps of taking the image and applying the heat can be performed, respectively, to carry out the steps of taking the image and applying the heat, respectively, without changing a relative positional relationship to each of parts to be detected, which are set on a continuous flat plane or a continuous curved plane for the detection object.

20. The crack detection system as claimed in claim 8, wherein:

said imaging unit and said heating unit are connected to each other so as to be movable in a united body relative to said part to be detected;

said heating unit is adapted to heat the part to be detected, from a side in a vicinity of the part to be detected on a side where the imaging unit is placed; and said imaging unit and said heating unit are movable relative to the detection object so as to reach sequentially positions in which steps of taking the image and applying the heat can be performed, respectively, to carry out the steps of taking the image and applying the heat, respectively, without changing a relative positional relationship to each of parts to be detected, which are set on a continuous flat plane or a continuous curved plane for the detection object.

21. The crack detection system as claimed in claim 9, wherein:

said imaging unit and said heating unit are connected to each other so as to be movable in a united body relative to said part to be detected;

said heating unit is adapted to heat the part to be detected, from a side in a vicinity of the part to be detected on a side where the imaging unit is placed; and said imaging unit and said heating unit are movable relative to the detection object so as to reach sequentially positions in which steps of taking the image and applying the heat can be performed, respectively, to carry out the steps of taking the image and applying the heat, respectively, without changing a relative positional relationship to each of parts to be detected, which are set on a continuous flat plane or a continuous curved plane for the detection object.

22. A crack detection method, which comprises the steps of:

taking, by a predetermined imaging unit, an image of an outermost coating surface of a predetermined part to be detected, of a detection object, which part comprises a main body formed of an conductive material and a coating layer formed of a non-conductive material, with which the main body is coated from outside;

applying heat to the part to be detected, the image of said coating surface of which has been taken, to increase a temperature of said coating layer to a predetermined temperature by which said coating layer may not degrade, by an induction heating applied to the part to be detected by means of a predetermined heating unit and/or a heat transfer in a vicinity of the part to be detected, along with the induction heating applied to the part to be detected;

taking an image of said coating surface of the part to be detected to which the heat has been applied, by means of said imaging unit once again; and determining, by a predetermined image analysis unit, strain by analysis from two images of the part to be detected, which have taken by said imaging unit before and after applying the heat, in respective positions of the part to be detected, to acquire a strain distribution in the part to be detected; and wherein: the strain distribution in the part to be detected includes, in a case where a crack exists in the part to be detected, a group of strains in which strains are concentrated almost linearly in a quite different form from other strains around the group of strains in the strain distribution, in response to a small displacement of an area with the crack due to application of the heat.

23. The crack detection method according to claim 22, wherein:
a depth of the crack or existence of penetration of the crack is detected from a magnitude of the strain for the group of strains in which the strains are concentrated almost linearly, in the strain distribution in the part to be detected, based on a relationship between a depth of a crack in a body formed of a same material as the detection object or the part to be detected of said detection object and a magnitude of the strain in the strain distribution corresponding to a position of said crack, both of which have previously been acquired.

* * * * *